(12) United States Patent
Beck-Sickinger et al.

(10) Patent No.: US 9,718,861 B2
(45) Date of Patent: Aug. 1, 2017

(54) POTENT LIGANDS OF THE GHRELIN RECEPTOR

(75) Inventors: Annette Beck-Sickinger, Leipzig (DE); Sylvia Els-Heindl, Leipzig (DE); Enrico Schild, Koethen (DE); Thue W. Schwartz, Frederiksberg (DK); Birgitte Holst Lange, Gentofte (DK)

(73) Assignee: Universitaet Leipzig, Leipzig (DE)

( * ) Notice: Subject to any disclaimer, the term of this patent is extended or adjusted under 35 U.S.C. 154(b) by 104 days.

(21) Appl. No.: 14/240,829

(22) PCT Filed: Aug. 24, 2012

(86) PCT No.: PCT/EP2012/066519
§ 371 (c)(1),
(2), (4) Date: Feb. 18, 2015

(87) PCT Pub. No.: WO2013/026927
PCT Pub. Date: Feb. 28, 2013

(65) Prior Publication Data
US 2015/0274781 A1    Oct. 1, 2015

(30) Foreign Application Priority Data

Aug. 25, 2011  (EP) ..................... 11178888

(51) Int. Cl.
 C07K 7/22  (2006.01)
(52) U.S. Cl.
 CPC ..................... *C07K 7/22* (2013.01)
(58) Field of Classification Search
 None
 See application file for complete search history.

(56) References Cited

PUBLICATIONS

Metabolic diseases facts, information, pictures | Encyclopedia.com articles about Metabolic diseases (Feb. 16, 2017) pp. 1-8.*
Sakurada T. et al., *Neuropeptides* (Apr. 1987), vol. 9(3): 197-206.
Sakurada T. et al., *European Journal of Pharmacology* (Dec. 1989), vol. 174(2-3): 153-160.
Chollet C. et al., *Journal of Peptide Science* (Nov. 2009), vol. 15(11): 711-730.
Holst B. et al., *Journal of Biological Chemistry* (May 2007), vol. 282(21): 15799-15811.
Holst B. et al., *Molecular Pharmacology* (Sep. 2006), vol. 70(3): 936-946.

* cited by examiner

*Primary Examiner* — Thomas S Heard
(74) *Attorney, Agent, or Firm* — Chalin A. Smith; Smith Patent, LLC

(57) ABSTRACT

The present invention relates to highly potent ligands at the ghrelin receptor to influence food intake or other conditions.

17 Claims, 4 Drawing Sheets

SEQUENCE LISTING

```
<160> NUMBER OF SEQ ID NOS: 25

<210> SEQ ID NO 1
<211> LENGTH: 5
<212> TYPE: PRT
<213> ORGANISM: Artificial Sequence
<220> FEATURE:
<223> OTHER INFORMATION: ghrelin receptor ligand-core peptide
<220> FEATURE:
<221> NAME/KEY: MISC_FEATURE
<222> LOCATION: (1)..(1)
<223> OTHER INFORMATION: Xaa means D-Trp
<220> FEATURE:
<221> NAME/KEY: MISC_FEATURE
<222> LOCATION: (3)..(3)
<223> OTHER INFORMATION: Xaa means D-Trp
<220> FEATURE:
<221> NAME/KEY: MOD_RES
<222> LOCATION: (5)..(5)
<223> OTHER INFORMATION: AMIDATION

<400> SEQUENCE: 1

Xaa Phe Xaa Leu Leu
1               5

<210> SEQ ID NO 2
<211> LENGTH: 6
<212> TYPE: PRT
<213> ORGANISM: Artificial Sequence
<220> FEATURE:
<223> OTHER INFORMATION: ghrelin receptor ligand; peptide 2
<220> FEATURE:
<221> NAME/KEY: MISC_FEATURE
<222> LOCATION: (2)..(2)
<223> OTHER INFORMATION: Xaa means D-Trp
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 2

Lys Xaa Phe Xaa Leu Leu
1               5

<210> SEQ ID NO 3
<211> LENGTH: 6
<212> TYPE: PRT
<213> ORGANISM: Artificial Sequence
<220> FEATURE:
<223> OTHER INFORMATION: ghrelin receptor ligand; peptide 3
<220> FEATURE:
<221> NAME/KEY: MISC_FEATURE
<222> LOCATION: (2)..(2)
<223> OTHER INFORMATION: Xaa means 1-naphthyl-D-alanine
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION
```

```
<400> SEQUENCE: 3

Lys Xaa Phe Xaa Leu Leu
1               5

<210> SEQ ID NO 4
<211> LENGTH: 6
<212> TYPE: PRT
<213> ORGANISM: Artificial Sequence
<220> FEATURE:
<223> OTHER INFORMATION: ghrelin receptor ligand; peptide 4
<220> FEATURE:
<221> NAME/KEY: MISC_FEATURE
<222> LOCATION: (2)..(2)
<223> OTHER INFORMATION: Xaa means beta-(3-benzothienyl)-D-alanine
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (4)..(4)
<223> OTHER INFORMATION: AMIDATION

<400> SEQUENCE: 4

Lys Xaa Phe Xaa Leu Leu
1               5

<210> SEQ ID NO 5
<211> LENGTH: 6
<212> TYPE: PRT
<213> ORGANISM: Artificial Sequence
<220> FEATURE:
<223> OTHER INFORMATION: ghrelin receptor ligand; peptide 5
<220> FEATURE:
<221> NAME/KEY: MISC_FEATURE
<222> LOCATION: (2)..(2)
<223> OTHER INFORMATION: Xaa means 3,3-diphenyl-D-alanine
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 5

Lys Xaa Phe Xaa Leu Leu
1               5

<210> SEQ ID NO 6
<211> LENGTH: 6
<212> TYPE: PRT
<213> ORGANISM: Artificial Sequence
<220> FEATURE:
<223> OTHER INFORMATION: ghrelin receptor ligand; peptide 19
<220> FEATURE:
<221> NAME/KEY: MISC_FEATURE
<222> LOCATION: (2)..(2)
<223> OTHER INFORMATION: Xaa means 1-naphthyl-D-alanine
<220> FEATURE:
<221> NAME/KEY: MISC_FEATURE
<222> LOCATION: (4)..(4)
<223> OTHER INFORMATION: Xaa means beta-(3-benzothienyl)-D-alanine
<220> FEATURE:
<221> NAME/KEY: MOD_RES
<222> LOCATION: (6)..(6)
<223> OTHER INFORMATION: AMIDATION

<400> SEQUENCE: 6

Lys Xaa Phe Xaa Leu Leu
1               5
```

```
<210> SEQ ID NO 7
<211> LENGTH: 6
<212> TYPE: PRT
<213> ORGANISM: Artificial Sequence
<220> FEATURE:
<223> OTHER INFORMATION: ghrelin receptor ligand; peptide 20
<220> FEATURE:
<221> NAME/KEY: MISC_FEATURE
<222> LOCATION: (2)..(2)
<223> OTHER INFORMATION: Xaa means beta-(3-benzothienyl)-D-alanine
<220> FEATURE:
<221> NAME/KEY: MISC_FEATURE
<222> LOCATION: (4)..(4)
<223> OTHER INFORMATION: Xaa means beta-(3-benzothienyl)-D-alanine
<220> FEATURE:
<221> NAME/KEY: MOD_RES
<222> LOCATION: (6)..(6)
<223> OTHER INFORMATION: AMIDATION

<400> SEQUENCE: 7

Lys Xaa Phe Xaa Leu Leu
1               5

<210> SEQ ID NO 8
<211> LENGTH: 6
<212> TYPE: PRT
<213> ORGANISM: Artificial Sequence
<220> FEATURE:
<223> OTHER INFORMATION: ghrelin receptor ligand; peptide 12
<220> FEATURE:
<221> NAME/KEY: MISC_FEATURE
<222> LOCATION: (2)..(2)
<223> OTHER INFORMATION: Xaa means D-Trp
<220> FEATURE:
<221> NAME/KEY: MISC_FEATURE
<222> LOCATION: (4)..(4)
<223> OTHER INFORMATION: Xaa means 1-naphthyl-D-alanine
<220> FEATURE:
<221> NAME/KEY: MOD_RES
<222> LOCATION: (6)..(6)
<223> OTHER INFORMATION: AMIDATION

<400> SEQUENCE: 8

Lys Xaa Phe Xaa Leu Leu
1               5

<210> SEQ ID NO 9
<211> LENGTH: 6
<212> TYPE: PRT
<213> ORGANISM: Artificial Sequence
<220> FEATURE:
<223> OTHER INFORMATION: ghrelin receptor ligand; peptide 13
<220> FEATURE:
<221> NAME/KEY: MISC_FEATURE
<222> LOCATION: (2)..(2)
<223> OTHER INFORMATION: Xaa means D-Trp
<220> FEATURE:
<221> NAME/KEY: MISC_FEATURE
<222> LOCATION: (4)..(4)
<223> OTHER INFORMATION: Xaa means 2-naphthyl-D-alanine
<220> FEATURE:
<221> NAME/KEY: MOD_RES
<222> LOCATION: (6)..(6)
<223> OTHER INFORMATION: AMIDATION

<400> SEQUENCE: 9

Lys Xaa Phe Xaa Leu Leu
1               5

<210> SEQ ID NO 10
<211> LENGTH: 6
```

```
<212> TYPE: PRT
<213> ORGANISM: Artificial Sequence
<220> FEATURE:
<223> OTHER INFORMATION: ghrelin receptor ligand; peptide 18
<220> FEATURE:
<221> NAME/KEY: MISC_FEATURE
<222> LOCATION: (2)..(2)
<223> OTHER INFORMATION: Xaa means 1-naphthyl-D-alanine
<220> FEATURE:
<221> NAME/KEY: MISC_FEATURE
<222> LOCATION: (4)..(4)
<223> OTHER INFORMATION: Xaa means 1-naphthyl-D-alanine
<220> FEATURE:
<221> NAME/KEY: MOD_RES
<222> LOCATION: (6)..(6)
<223> OTHER INFORMATION: AMIDATION

<400> SEQUENCE: 10

Lys Xaa Phe Xaa Leu Leu
1               5

<210> SEQ ID NO 11
<211> LENGTH: 6
<212> TYPE: PRT
<213> ORGANISM: Artificial Sequence
<220> FEATURE:
<223> OTHER INFORMATION: ghrelin receptor ligand; peptide 6
<220> FEATURE:
<221> NAME/KEY: MISC_FEATURE
<222> LOCATION: (2)..(2)
<223> OTHER INFORMATION: Xaa means D-2-Nal
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 11

Lys Xaa Phe Xaa Leu Leu
1               5

<210> SEQ ID NO 12
<211> LENGTH: 6
<212> TYPE: PRT
<213> ORGANISM: Artificial Sequence
<220> FEATURE:
<223> OTHER INFORMATION: ghrelin receptor ligand; peptide 7
<220> FEATURE:
<221> NAME/KEY: MISC_FEATURE
<222> LOCATION: (2)..(2)
<223> OTHER INFORMATION: Xaa means D-Bpa
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 12

Lys Xaa Phe Xaa Leu Leu
1               5

<210> SEQ ID NO 13
<211> LENGTH: 6
<212> TYPE: PRT
<213> ORGANISM: Artificial Sequence
<220> FEATURE:
<223> OTHER INFORMATION: ghrelin receptor ligand; peptide 8
```

```
-continued

<220> FEATURE:
<221> NAME/KEY: MISC_FEATURE
<222> LOCATION: (2)..(2)
<223> OTHER INFORMATION: Xaa means D-Bip
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 13

Lys Xaa Phe Xaa Leu Leu
1               5

<210> SEQ ID NO 14
<211> LENGTH: 6
<212> TYPE: PRT
<213> ORGANISM: Artificial Sequence
<220> FEATURE:
<223> OTHER INFORMATION: ghrelin receptor ligand;peptide 9
<220> FEATURE:
<221> NAME/KEY: MISC_FEATURE
<222> LOCATION: (2)..(2)
<223> OTHER INFORMATION: Xaa means D-Phe
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 14

Lys Xaa Phe Xaa Leu Leu
1               5

<210> SEQ ID NO 15
<211> LENGTH: 6
<212> TYPE: PRT
<213> ORGANISM: Artificial Sequence
<220> FEATURE:
<223> OTHER INFORMATION: ghrelin receptor ligand; peptide 10
<220> FEATURE:
<221> NAME/KEY: MISC_FEATURE
<222> LOCATION: (2)..(2)
<223> OTHER INFORMATION: Xaa means D-tBf
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 15

Lys Xaa Phe Xaa Leu Leu
1               5

<210> SEQ ID NO 16
<211> LENGTH: 6
<212> TYPE: PRT
<213> ORGANISM: Artificial Sequence
<220> FEATURE:
<223> OTHER INFORMATION: ghrelin receptor ligand; peptide 11
<220> FEATURE:
<221> NAME/KEY: MISC_FEATURE
<222> LOCATION: (2)..(2)
<223> OTHER INFORMATION: Xaa means D-Trp(Me)
```

```
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 16

Lys Xaa Phe Xaa Leu Leu
1               5

<210> SEQ ID NO 17
<211> LENGTH: 6
<212> TYPE: PRT
<213> ORGANISM: Artificial Sequence
<220> FEATURE:
<223> OTHER INFORMATION: ghrelin receptor ligand; peptide 14
<220> FEATURE:
<221> NAME/KEY: MISC_FEATURE
<222> LOCATION: (2)..(2)
<223> OTHER INFORMATION: Xaa means D-Trp
<220> FEATURE:
<221> NAME/KEY: MISC_FEATURE
<222> LOCATION: (4)..(4)
<223> OTHER INFORMATION: Xaa means D-Bip
<220> FEATURE:
<221> NAME/KEY: MOD_RES
<222> LOCATION: (6)..(6)
<223> OTHER INFORMATION: AMIDATION

<400> SEQUENCE: 17

Lys Xaa Phe Xaa Leu Leu
1               5

<210> SEQ ID NO 18
<211> LENGTH: 6
<212> TYPE: PRT
<213> ORGANISM: Artificial Sequence
<220> FEATURE:
<223> OTHER INFORMATION: ghrelin receptor ligand; peptide 15
<220> FEATURE:
<221> NAME/KEY: MISC_FEATURE
<222> LOCATION: (2)..(2)
<223> OTHER INFORMATION: Xaa means D-Trp
<220> FEATURE:
<221> NAME/KEY: MISC_FEATURE
<222> LOCATION: (4)..(4)
<223> OTHER INFORMATION: Xaa means D-Bpa
<220> FEATURE:
<221> NAME/KEY: MOD_RES
<222> LOCATION: (6)..(6)
<223> OTHER INFORMATION: AMIDATION

<400> SEQUENCE: 18

Lys Xaa Phe Xaa Leu Leu
1               5

<210> SEQ ID NO 19
<211> LENGTH: 6
<212> TYPE: PRT
<213> ORGANISM: Artificial Sequence
<220> FEATURE:
<223> OTHER INFORMATION: ghrelin receptor ligand; peptide 16
<220> FEATURE:
<221> NAME/KEY: MISC_FEATURE
<222> LOCATION: (2)..(2)
<223> OTHER INFORMATION: Xaa means D-Trp
<220> FEATURE:
<221> NAME/KEY: MISC_FEATURE
<222> LOCATION: (4)..(4)
<223> OTHER INFORMATION: Xaa means D-Dip
```

```
<220> FEATURE:
<221> NAME/KEY: MOD_RES
<222> LOCATION: (6)..(6)
<223> OTHER INFORMATION: AMIDATION

<400> SEQUENCE: 19

Lys Xaa Phe Xaa Leu Leu
1               5

<210> SEQ ID NO 20
<211> LENGTH: 6
<212> TYPE: PRT
<213> ORGANISM: Artificial Sequence
<220> FEATURE:
<223> OTHER INFORMATION: ghrelin receptor ligand; peptide 17
<220> FEATURE:
<221> NAME/KEY: MISC_FEATURE
<222> LOCATION: (2)..(2)
<223> OTHER INFORMATION: Xaa means D-Trp
<220> FEATURE:
<221> NAME/KEY: MISC_FEATURE
<222> LOCATION: (4)..(4)
<223> OTHER INFORMATION: Xaa means D-Bth
<220> FEATURE:
<221> NAME/KEY: MOD_RES
<222> LOCATION: (6)..(6)
<223> OTHER INFORMATION: AMIDATION

<400> SEQUENCE: 20

Lys Xaa Phe Xaa Leu Leu
1               5

<210> SEQ ID NO 21
<211> LENGTH: 6
<212> TYPE: PRT
<213> ORGANISM: Artificial Sequence
<220> FEATURE:
<223> OTHER INFORMATION: ghrelin receptor ligand; peptide 21
<220> FEATURE:
<221> NAME/KEY: MISC_FEATURE
<222> LOCATION: (2)..(2)
<223> OTHER INFORMATION: Xaa means D-1-Nal
<220> FEATURE:
<221> NAME/KEY: MISC_FEATURE
<222> LOCATION: (3)..(3)
<223> OTHER INFORMATION: Xaa means Cha
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 21

Lys Xaa Xaa Xaa Leu Leu
1               5

<210> SEQ ID NO 22
<211> LENGTH: 6
<212> TYPE: PRT
<213> ORGANISM: Artificial Sequence
<220> FEATURE:
<223> OTHER INFORMATION: ghrelin receptor ligand; peptide 22
<220> FEATURE:
<221> NAME/KEY: MISC_FEATURE
<222> LOCATION: (2)..(2)
<223> OTHER INFORMATION: Xaa means D-1-Nal
<220> FEATURE:
<221> NAME/KEY: MISC_FEATURE
<222> LOCATION: (3)..(3)
<223> OTHER INFORMATION: Xaa means L-tBf
```

```
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 22

Lys Xaa Xaa Xaa Leu Leu
1               5

<210> SEQ ID NO 23
<211> LENGTH: 6
<212> TYPE: PRT
<213> ORGANISM: Artificial Sequence
<220> FEATURE:
<223> OTHER INFORMATION: ghrelin receptor ligand; peptide 23
<220> FEATURE:
<221> NAME/KEY: MISC_FEATURE
<222> LOCATION: (2)..(2)
<223> OTHER INFORMATION: Xaa means D-1-Nal
<220> FEATURE:
<221> NAME/KEY: MISC_FEATURE
<222> LOCATION: (3)..(3)
<223> OTHER INFORMATION: Xaa means D-Phe
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 23

Lys Xaa Xaa Xaa Leu Leu
1               5

<210> SEQ ID NO 24
<211> LENGTH: 6
<212> TYPE: PRT
<213> ORGANISM: Artificial Sequence
<220> FEATURE:
<223> OTHER INFORMATION: ghrelin receptor ligand; peptide 24
<220> FEATURE:
<221> NAME/KEY: MISC_FEATURE
<222> LOCATION: (2)..(2)
<223> OTHER INFORMATION: Xaa means D-1-Nal
<220> FEATURE:
<221> NAME/KEY: MISC_FEATURE
<222> LOCATION: (3)..(3)
<223> OTHER INFORMATION: Xaa means L-Nva
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 24

Lys Xaa Xaa Xaa Leu Leu
1               5

<210> SEQ ID NO 25
<211> LENGTH: 6
<212> TYPE: PRT
<213> ORGANISM: Artificial Sequence
<220> FEATURE:
<223> OTHER INFORMATION: ghrelin receptor ligand; peptide 25
```

```
<220> FEATURE:
<221> NAME/KEY: MISC_FEATURE
<222> LOCATION: (2)..(2)
<223> OTHER INFORMATION: Xaa means D-1-Nal
<220> FEATURE:
<221> NAME/KEY: MISC_FEATURE
<222> LOCATION: (3)..(3)
<223> OTHER INFORMATION: Xaa means L-Phg
<220> FEATURE:
<221> NAME/KEY: MISC_FEATURE
<222> LOCATION: (4)..(4)
<223> OTHER INFORMATION: Xaa means D-Trp
<220> FEATURE:
<221> NAME/KEY: MOD_RES
<222> LOCATION: (6)..(6)
<223> OTHER INFORMATION: AMIDATION

<400> SEQUENCE: 25

Lys Xaa Xaa Xaa Leu Leu
1               5
```

POTENT LIGANDS OF THE GHRELIN RECEPTOR

This application corresponds to the national phase of International Application No. PCT/EP2012/066519 filed Aug. 24, 2012 which, in turn, claims priority to European Patent Application No. 11.178888.1 filed Aug. 25, 2011, the contents of which are incorporated by reference herein in their entirety.

FIELD OF THE INVENTION

The present invention relates to highly potent ligands at the ghrelin receptor to influence food intake.

BACKGROUND OF THE INVENTION

The ghrelin receptor is a typical rhodopsin receptor-like G protein-coupled receptor and was identified 1996 as the growth hormone secretagogue receptor GHS-R1a[1]. Although involved in the control of growth hormone secretion, the endogenous ligand ghrelin has potent orexigenic effects and stimulates food intake[2,3]. The major target for ghrelin is the hypothalamus, where the ghrelin receptor is mainly expressed in the NPY/AgRP neurons of the arcuate nucleus[4], the center for energy homeostasis. Furthermore, a high ghrelin receptor expression is observed in the ventromedial nucleus of the hypothalamus. This region is considered to be the regulation center for fatty acid metabolism[5,6].

The ghrelin receptor possesses an exceptionally high constitutive activity. It was suggested to induce constant appetite and to trigger food intake in between meals[7,8]. In this context, reducing the basal activity of the ghrelin receptor could be an innovative and efficient strategy for obesity treatment[9]. Indeed, the increasing problem of obesity, not only in high-income states but also in low- and middle-income countries, urges the development of anti-obesity drugs[10]. Currently, treatments are restricted to only few pharmaceuticals, most presenting moderate benefits, poor tolerance and strong side effects[11-13]. Although lifestyle changes are mandatory for significant weight loss, bariatric surgery is considered to be the only effective treatment against morbid obesity. However, surgery presented high risks, high costs and always requires highly qualified performers[14]. Interestingly, the reason of sustainable weight loss after bariatric surgery is suggested to be due to a modification of gut hormone levels[15]. Thus, a specific inverse agonist able to reduce basal signaling of the ghrelin receptor and therefore, appetite and food intake in between meals could be in fact an efficient pharmaceutical against obesity.

A modified analog of substance P, [D-Arg[1], D-Phe[5], D-Trp[7,9], Leu[11]]-substance P (MSP), was the first described ghrelin receptor inverse agonist (FIG. 1). MSP acts as a partial antagonist, but more importantly as an inverse agonist at the ghrelin receptor inhibiting the spontaneous, ligand-independent signaling[16]. Extensive structure-activity relationship (SAR) studies followed this discovery. After systematic truncation of the N-terminus of MSP, the C-terminal heptapeptide fQwFwLL-NH$_2$ was identified as the minimal sequence able to act at the ghrelin receptor with inverse agonist properties. Affinity and activity were decreased 5.3-fold and 1.6-fold, respectively, in comparison to the full-length modified substance P. In addition, the pentapeptide wFwLL-NH$_2$ (SEQ ID NO:1) is the minimal sequence able to bind the receptor (IC$_{50}$=530±230 nM)[17]. This compound showed a biphasic concentration-response curve. It acts as a partial agonist at low peptide concentrations and as an inverse agonist at concentrations higher than 1 nM. Interestingly, this dual response could be modulated by modification of chemophysical properties at the N-terminus. Introduction of a positively charged amino acid (Lys or Arg) led to highly potent inverse agonists (EC$_{50}$=36±8 and 21±2, respectively), whereas introduction of a neutral amino acid such as Ala revealed a highly potent agonist[18]. In addition, the aromatic core wFw appeared to be crucial for receptor binding[17]. Ala-scan of MSP demonstrated that substitution of both D-tryptophanes with L-alanine resulted in a total loss of activity and substitution of L-phenylalanine produced a 10-fold decrease in the inverse agonist activity.

There is a need for highly potent inverse agonists with high efficacy that may be useful in the treatment of feeding-related disorders. The inventors of this application surprisingly found that modification of the D-tryptophane at position 2 ('w[2]') in the peptide sequence KwFwLL-NH$_2$ (SEQ ID NO:2) resulted in peptides which inhibited the ghrelin receptor more strongly than the basic peptide KwFwLL-NH$_2$ (see Table 2 and FIG. 3). That is, the modified peptides had a higher efficacy. It was further found that the phenylalanine is essential for inverse agonistic activity (see Table 5 and FIG. 6) and that modification of D-tryptophane at position 4 ('w[4]') in the peptide sequence KwFwLL-NH$_2$ (SEQ ID NO:2) resulted in peptides having agonistic properties.

SUMMARY OF THE INVENTION

In a first aspect, the present invention therefore relates to a peptide comprising, or substantially consisting of, the amino acid sequence

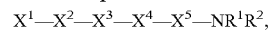

wherein $X^1$ represents an amino acid selected from the group consisting of Lys and Arg, $X^2$ and $X^4$ each independently represents an aromatic amino acid, with at least one of $X^2$ and $X^4$ being different from D- and L-tryptophane, $X^3$ represents a hydrophobic amino acid, $X^5$ represents Leu-Leu; and $R^1$ and $R^2$ each independently is hydrogen or an optionally substituted hydrocarbon group;

or $R^1$ and $R^2$ together with the nitrogen atom to which they are attached form a 5- or 6-membered ring.

In a second aspect, the invention relates to a peptide comprising, or substantially consisting of, the amino acid sequence

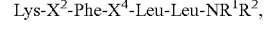

wherein $X^2$ and $X^4$ each independently is an aromatic amino acid, with at least one of $X^2$ and $X^4$ being different from D- and L-tryptophane, $R^1$ and $R^2$ each independently is hydrogen or an optionally substituted hydrocarbon group;

or $R^1$ and $R^2$ together with the nitrogen atom to which they are attached form a 5- or 6-membered ring.

In another aspect, the invention relates to a peptide according to the present invention for use in the treatment or prophylaxis of a condition selected from the group consisting of metabolic and/or endocrine disorders, obesity and obesity-associated disorders, appetite or eating disorders, addictive disorders, cardiovascular disorders, gastrointestinal disorders, cirrhosis, chronic liver disease and combinations thereof.

In yet another aspect the invention relates to the use of a peptide according to the present invention for the manufacture of a medicament for the treatment or prophylaxis of a condition selected from the group consisting of metabolic and/or endocrine disorders, obesity and obesity-associated disorders, appetite or eating disorders, addictive disorders, cardiovascular disorders, gastrointestinal disorders, cirrhosis, chronic liver disease and combinations thereof.

In yet another aspect, the invention pertains to a method for treating a condition selected from the group consisting of metabolic and/or endocrine disorders, obesity and obesity-associated disorders, appetite or eating disorders, addictive disorders, cardiovascular disorders, gastrointestinal disorders, cirrhosis, chronic liver disease and combinations thereof, said method comprising administering to an individual a pharmaceutically effective dose of a peptide of the present invention.

In particular, the present invention relates to the following items [1] to [19].

[1] A peptide comprising, or consisting of, the amino acid sequence $X^1$—$X^2$—$X^3$—$X^4$—$X^5$—$NR^1R^2$, wherein
- $X^1$ represents an amino acid selected from the group consisting of Gln, Lys and Arg;
- $X^2$ and $X^4$ each independently represents an aromatic amino acid, with at least one of $X^2$ and $X^4$ being different from D- and L-tryptophane;
- $X^3$ represents a hydrophobic amino acid;
- $X^5$ represents Leu-Leu; and
- $R^1$ and $R^2$ each independently is hydrogen or an optionally substituted hydrocarbon group; or $R^1$ and $R^2$ together with the nitrogen atom to which they are attached form a 5- or 6-membered ring;

and wherein said peptide is preferably capable of increasing or decreasing the constitutive activity of a ghrelin receptor by at least 10%, when contacted with the ghrelin receptor at a concentration of $10^{-7}$ M in an inositol turnover assay in COS-7 cells expressing the ghrelin receptor.

[2] The peptide of item [1], wherein $X^2$ represents an amino acid comprising a bicyclic or dicyclic aromatic side chain, preferably an amino acid of formula (I)

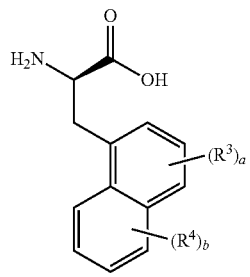

wherein
- each $R^3$ independently is halogen, hydroxyl, CN, $C_1$-$C_2$-alkyl, $C_1$-$C_2$-alkoxy, C(O)—$C_1$-$C_2$-alkyl, C(O)—$C_1$-$C_2$-alkoxy, C(O)NH$_2$, C(O)NH—$C_1$-$C_4$-alkyl, $C_1$-$C_2$-alkyl substituted by halogen;
- each $R^4$ independently is is halogen, hydroxyl, CN, $C_1$-$C_4$-alkyl, $C_1$-$C_4$-alkoxy, C(O)—$C_1$-$C_4$-alkyl, C(O)—$C_1$-$C_4$-alkoxy, C(O)NH$_2$, C(O)NH—$C_1$-$C_4$-alkyl, $C_1$-$C_2$-alkyl substituted by halogen, SO$_2$NH$_2$, SO$_2$NH—$C_1$-$C_4$-alkyl;
- a is 0, 1, 2;
- b is 0, 1, 2, 3, 4;

an amino acid of formula (II)

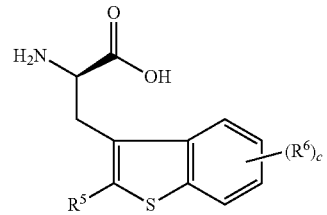

wherein
- $R^5$ is hydrogen, halogen, hydroxyl, CN, $C_1$-$C_2$-alkyl, $C_1$-$C_2$-alkoxy, C(O)—$C_1$-$C_2$-alkyl, C(O)—$C_1$-$C_2$-alkoxy, C(O)NH$_2$, C(O)NH—$C_1$-$C_4$-alkyl, $C_1$-$C_2$-alkyl substituted by halogen;
- each $R^6$ independently is halogen, hydroxyl, CN, $C_1$-$C_4$-alkyl, $C_1$-$C_4$-alkoxy, C(O)—$C_1$-$C_4$-alkyl, C(O)—$C_1$-$C_4$-alkoxy, C(O)NH$_2$, C(O)NH—$C_1$-$C_4$-alkyl, $C_1$-$C_2$-alkyl substituted by halogen, SO$_2$NH$_2$, SO$_2$NH—$C_1$-$C_4$-alkyl;
- c is 0, 1, 2, 3, 4;

an amino acid of formula (III)

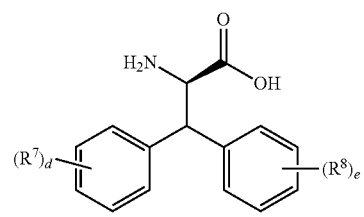

wherein
- each $R^7$ independently is halogen, hydroxyl, CN, $C_1$-$C_4$-alkyl, $C_1$-$C_4$-alkoxy, C(O)—$C_1$-$C_4$-alkyl, C(O)—$C_1$-$C_4$-alkoxy, C(O)NH$_2$, C(O)NH—$C_1$-$C_4$-alkyl, $C_1$-$C_2$-alkyl substituted by halogen, SO$_2$NH$_2$, SO$_2$NH—$C_1$-$C_4$-alkyl;
- each $R^8$ independently is halogen, hydroxyl, CN, $C_1$-$C_4$-alkyl, $C_1$-$C_4$-alkoxy, C(O)—$C_1$-$C_4$-alkyl, C(O)—$C_1$-$C_4$-alkoxy, C(O)NH$_2$, C(O)NH—$C_1$-$C_4$-alkyl, $C_1$-$C_2$-alkyl substituted by halogen, SO$_2$NH$_2$, SO$_2$NH—$C_1$-$C_4$-alkyl;
- d is 0, 1, 2, 3, 4, 5;
- e is 0, 1, 2, 3, 4, 5;

an amino acid of formula (IV)

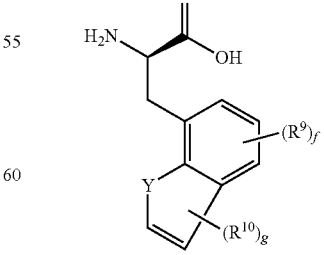

wherein
- each $R^9$ independently is halogen, hydroxyl, CN, $C_1$-$C_2$-alkyl, $C_1$-$C_2$-alkoxy, C(O)—$C_1$-$C_2$-alkyl, C(O)—$C_1$-$C_2$- alkoxy, C(O)NH$_2$, C(O)NH—C$_1$-C$_4$-alkyl, C$_1$-C$_2$-alkyl substituted by halogen, SO$_2$NH$_2$, SO$_2$NH—C$_1$-C$_2$-alkyl;
each R$^{10}$ independently is halogen, hydroxyl, CN, C$_1$-C$_4$-alkyl, C$_1$-C$_4$-alkoxy, C(O)—C$_1$-C$_4$-alkyl, C(O)—C$_1$-C$_4$-alkoxy, C(O)NH$_2$, C(O)NH—C$_1$-C$_4$-alkyl, C$_1$-C$_2$-alkyl substituted by halogen, SO$_2$NH$_2$, SO$_2$NH—C$_1$-C$_4$-alkyl;
Y is O, S, NH, N—C$_1$-C$_4$-alkyl or CH$_2$;
f is 0, 1, 2, 3;
g is 0, 1, 2;
or an amino acid of formula (V)

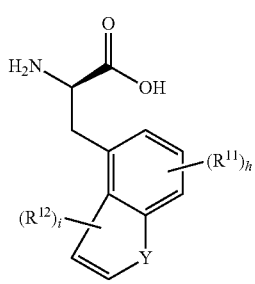 (V)

wherein
each R$^{11}$ independently is halogen, hydroxyl, CN, C$_1$-C$_2$-alkyl, C$_1$-C$_2$-alkoxy, C(O)—C$_1$-C$_2$-alkyl, C(O)—C$_1$-C$_2$-alkoxy, C(O)NH$_2$, C(O)NH—C$_1$-C$_4$-alkyl, C$_1$-C$_2$-alkyl substituted by halogen, SO$_2$NH$_2$, SO$_2$NH—C$_1$-C$_2$-alkyl;
each R$^{12}$ independently is halogen, hydroxyl, CN, C$_1$-C$_4$-alkyl, C$_1$-C$_4$-alkoxy, C(O)—C$_1$-C$_4$-alkyl, C(O)—C$_1$-C$_4$-alkoxy, C(O)NH$_2$, C(O)NH—C$_1$-C$_4$-alkyl, C$_1$-C$_2$-alkyl substituted by halogen, SO$_2$NH$_2$, SO$_2$NH—C$_1$-C$_4$-alkyl;
Y is O, S, NH, N—C$_1$-C$_4$-alkyl or CH$_2$;
h is 0, 1, 2, 3;
i is 0, 1, 2.

[3] The peptide of item [1], wherein X$^2$ is selected from the group consisting of 1-naphthyl-D-alanine, β-(3-benzothienyl)-D-alanine and 3,3-diphenyl-D-alanine.

[4] The peptide of any one of items [1] to [3], wherein X$^4$ is selected from the group consisting of D-tryptophane, 1-naphthyl-D-alanine, 2-naphthyl-D-alanine and β-(3-benzothienyl)-D-alanine.

[5] The peptide of any one of items [1] to [4], wherein X$^2$ is D-tryptophane.

[6] The peptide of any one of items [1] to [4], wherein X$^4$ is D-tryptophane.

[7] The peptide of any one of the preceding items, wherein X$^1$ is Lys.

[8] The peptide of any one of the preceding items, wherein X$^3$ is Phe.

[9] The peptide of any one of the preceding items, which increases or inhibits the constitutive activity of ghrelin receptor with an EC$_{50}$ value of less than 10$^{-7}$ M, as determined in an inositol turnover assay in COS-7 cells transfected with the ghrelin receptor.

[10] The peptide of any one of the preceding items, which is capable of decreasing the constitutive activity of ghrelin receptor by at least 25% at a concentration of 10$^{-7}$ M.

[11] The peptide of item [10], comprising an amino acid sequence selected from the group consisting of SEQ ID NO:3, 4, 5, 6 and 7.

[12] The peptide of item [10] or [11], which is capable of reducing the food intake of a mammal when administered to said mammal.

[13] The peptide of any one of items [1] to [9], which is capable of increasing the constitutive activity of ghrelin receptor by at least 25% at a concentration of 10$^{-7}$ M.

[14] The peptide of item [11], comprising an amino acid sequence selected from the group consisting of SEQ ID NO:8 or 9.

[15] The peptide of item [13] or [14], which is capable of promoting the appetite of a mammal when administered to said mammal.

[16] The peptide as defined in any one of the preceding items for use in the treatment or prophylaxis of a condition selected from the group consisting of metabolic and/or endocrine disorders, obesity and obesity-associated disorders, appetite or eating disorders, addictive disorders, cardiovascular disorders, gastrointestinal disorders, cirrhosis, chronic liver disease and combinations thereof.

[17] The peptide of item [16], wherein said condition is selected from the group consisting of obesity, overweight, metabolic syndrome, insulin resistance, dyslipidemia, impaired glucose tolerance and hypertension.

[18] The peptide of item [16], wherein said condition is anorexia and/or abnormally reduced food intake behaviour.

[19] A pharmaceutical composition comprising the peptide according to any one of items [1] to [15].

DETAILED DESCRIPTION

Definitions

Figure 1:
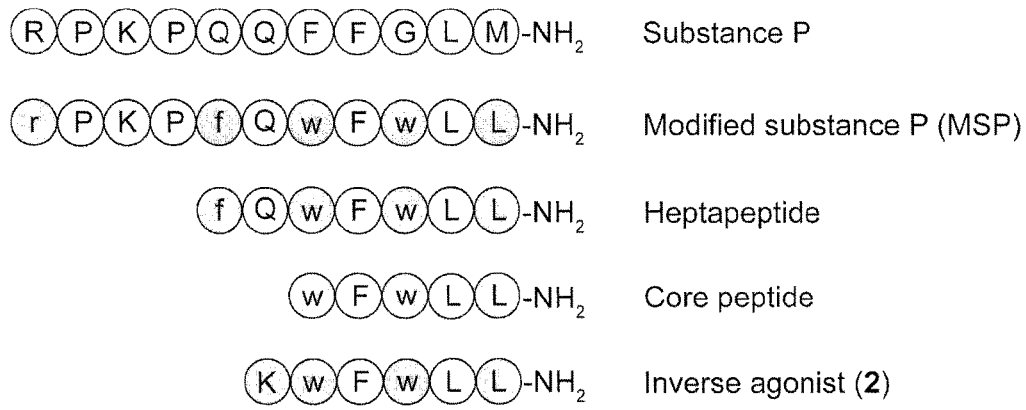
FIG. 1: Summary of SAR studies leading to the identification of short potent inverse agonists. The analog [D-Arg$^1$, D-Phe$^5$, D-Trp$^{7,9}$, Leu$^{11}$]-Substance P is able to act on the ghrelin receptor as a moderate inverse agonist. Truncation of the N-terminus revealed the heptapeptide that showed similar activity and affinity as the full-length peptide and led to the core peptide, the shortest sequence able to bind the receptor. Addition of a positively charged amino acid at the N-terminus led to the potent ghrelin receptor inverse agonist KwFwLL-NH$_2$ (2). Hereby, we modified the aromatic peptide core and investigated the influence towards activity and efficacy.

Unless otherwise stated, the following terms used in the specification and claims have the meanings given below.

A "peptide" as used herein is defined as a chemical compound comprised of two or more amino acids covalently bound together, or a salt thereof. The amino acids of the peptide can be D- and/or L-α-amino acids, β-amino acids as well as other organic compounds containing at least one primary and/or secondary amino group and at least one carboxylic acid group. Preferably, the amino acids of the peptide of the present invention are α-amino acids.

A "ligand" as used herein is intended to mean a substance that either inhibits or stimulates the activity of a receptor and/or that competes for the receptor in a binding assay.

The "constitutive activity" of a receptor—in this case the ghrelin receptor—is defined as the signalling activity of the receptor in the absence of any ligand. Unless otherwise indicated herein, the "activity" of the ghrelin receptor refers to inositol phosphate turnover as a measure of G-protein signalling through the phospholipase C pathway, see example. It can be determined as described infra.

An "agonist" is defined as a ligand increasing the functional activity of a receptor. An agonist of the ghrelin receptor is a ligand increasing the constitutive functional activity of the ghrelin receptor.

An "inverse agonist" is defined as a ligand decreasing the constitutive functional activity of the receptor (here: the ghrelin receptor) in the absence of other ligands. The term also includes partial inverse agonists, which only decrease the basal activity of the receptor to a certain level and not entirely. It should be noted that certain compounds could be both an inverse agonist (in the absence of any hormone) and an antagonist (in the presence of the hormone).

An "antagonist" is defined as a ligand decreasing the functional activity of a receptor (here: the ghrelin receptor) by inhibiting the action of an agonist. Antagonism usually is a property of the ligand measured in the presence of an agonist.

The inverse agonistic or agonistic activity of the peptide of the invention can be determined in a cell culture assay using an inositol turnover assay in COS-7 cells transfected with the ghrelin receptor. Most preferably, the inositol turnover assay is performed exactly as carried out in the examples of the present invention. A shortened protocol for stably transfected cells is as follows:

COS-7 cells stably transfected with human ghrelin receptor cDNA are cultured in a humidified atmosphere at 37° C. and 5% $CO_2$ in Dulbecco's modified Eagle's medium with higher glucose supplemented with 10% (v/v) FCS and 1% (v/v) penicillin/streptomycin and 0.4 mg/ml hygromycin B.

The stable cells are seeded out in 24-well plates (80.000-100.000 cells/well) in DMEM with 10% FCS and 0.4 mg/ml hygromycin B.

The day after seeding the stable cells, cells are incubated with myo-[2-$^3$H]-inositol (2 μCi/ml) for 18 h and washed with DMEM/LiCl.

Stimulation is then carried out with seven to nine different peptide concentrations in DMEM containing 10 mM LiCl, for 2 h, in duplicates.

Stimulation is stopped by aspirating the medium and, subsequently, cells are lysed with 150 μl of 0.1M NaOH for 5 min at RT.

50 μl of 0.2M HCOOH are added and the solution is diluted using 1 ml dilution buffer.

After removing cell debris, the supernatant is purified on an anion-exchange resin.

Obtained data are analyzed and dpm values are assigned to the corresponding peptide concentrations.

Non-linear regression may be used to obtain sigmoidal curves.

For better comparability, dpm values may be normalized to the constitutive activity.

Unless indicated otherwise, all indications of ghrelin receptor activity or "efficacy" refer to this assay.

The cDNA encoding human ghrelin receptor has been cloned, Genbank accession no. U60179. The protein sequence can be found in SwissProt entry Q92847, GHSR_HUMAN. The ghrelin receptor used in the methods according to the invention can be the human ghrelin receptor (SwissProt entry Q92847), any orthologue thereof such as a non-human ghrelin receptor such as the murine (SwissProt entry Q99P50), the rat (SwissProt entry O08725), the rabbit (SwissProt entry A5A4K9), the pig (SwissProt entry Q95254), and a primate ghrelin receptor, and any genetic or allelic variants thereof. Preferably the ghrelin receptor is the human ghrelin receptor, or a variant thereof such as a polypeptide having an amino acid sequence which has a sequence identity of more than 80%, such as more than 85%, preferably more than 90%, or even more preferably more than 95%, compared to sequence of the human ghrelin receptor SwissProt entry Q92847, including a fragment of such a polypeptide able to bind ghrelin, or a polypeptide comprising such a fragment, such as a fusion protein.

The term "efficacy" of a peptide ($E_{max}$) is the difference between constitutive activity of the ghrelin receptor and its activity at maximal effect of the peptide. $EC_{50}$ is the peptide concentration at half-maximal effect.

The term "$EC_{50}$ for inverse agonism" denotes the concentration of a compound (inverse agonist) required to obtain 50% maximum achievable inverse agonistic activity for that compound, i.e. the concentration required to decrease the constitutive activity of the ghrelin receptor by 50% of the maximum achievable decrease in activity (maximum achievable inverse agonistic response) provided by the inverse agonist. For a full inverse agonist $EC_{50}$ for inverse agonism is the concentration of inverse agonist, which decreases the constitutive activity of the ghrelin receptor by 50%. For an 80% partial inverse agonist it is the concentration of inverse agonist, which decreases the constitutive activity of the ghrelin receptor by 40%, i.e. down to 60% of the constitutive activity.

The term "$EC_{50}$ for agonism" denotes the concentration of a compound required to obtain 50% maximum achievable agonistic activity for that compound, i.e. the concentration of compound required to increase the constitutive activity of the ghrelin receptor up to 50% of the maximally achievable increase obtainable with that compound.

As used herein, the term "body mass index" or "BMI" is defined as follows:

$$BMI = \frac{mass(kg)}{(height(m))^2}$$

The present invention relates to peptide compounds that exhibit inverse agonistic or agonistic activity at the ghrelin receptor.

The term "halogen" refers to one or several fluoro, chloro, bromo, or iodo substituents. Preferably the term "halogen" refers to one or several fluoro, chloro substituents, whereby one or several fluoro substituents are particularly preferred.

The term "alkyl" refers to a linear saturated hydrocarbon substituent having one to four carbon atoms or a branched saturated hydrocarbon substituent having three to four carbon atoms, e. g., methyl, ethyl, n-propyl, 2-propyl, n-butyl, tert-butyl and the like. Thus, the term "$C_1$-$C_2$-alkyl" refers to methyl and ethyl and the term "$C_1$-$C_4$-alkyl" preferably refers to methyl, ethyl and 2-propyl.

The term "alkoxy" refers to a substituent —O-alkyl, wherein the term "alkyl" is as defined above. Thus, the term "$C_1$-$C_2$-alkoxyl" refers to methoxyl and ethoxy and the term "$C_1$-$C_4$-alkyl" preferably refers to methoxy, ethoxy and 2-propoxy.

The term "C(O)-alkyl" refers to a substituent in which the term "alkyl" is as defined above. Preferred forms of C(O)-alkyl are acetyl and propionyl.

The term "C(O)-alkoxy" refers to an ester substituent C(O)O-alkyl in which the term "alkyl" is as defined above. Thus, the term "C(O)—$C_1$-$C_2$-alkoxy" refers to the corresponding methyl and ethyl ester substituents and the term "C(O)—$C_1$-$C_4$-alkoxy" preferably refers to the corresponding methyl, ethyl and 2-propyl ester substituents.

The terms "C(O)—$NH_2$" and "C(O)NH-alkyl" refer to amide substituents in which the term "alkyl" is as defined above. Thus, the term "C(O)—NH—$C_1$-$C_2$-alkyl" refers to a substituent having a N-methyl or a N-ethyl substituent and the term "C(O)—NH—$C_1$-$C_4$-alkyl" preferably refers to a substituent having a N-methyl, a N-ethyl or a N-2-propyl substituents.

The term "alkyl substituted by halogen" refers to a substituent in which the term "alkyl" is as defined above. Preferably the term "halogen" refers to one or several fluoro substituents. In a particularly preferred embodiment of the present invention the terms "$C_1$-$C_2$-alkyl substituted by halogen" "$C_1$-$C_4$-alkyl substituted by halogen" refer to a trifluoromethyl substituent.

The terms "$SO_2NH_2$" and "$SO_2NH$-alkyl" refer to sulfoamide substituents in which the term "alkyl" is as defined above. Thus, the term "$SO_2NH$—$C_1$-$C_2$-alkyl" refers to a substituent having an N-methyl or an N-ethyl substituent and the term "$SO_2NH$—$C_1$-$C_4$-alkyl" preferably refers to a substituent having an N-methyl, an N-ethyl or an N-2-propyl substituent.

The term "optionally substituted hydrocarbon group" refers to an alkyl substituent as defined above which is optionally substituted independently with one to four substituents, preferably one or two substituents selected from alkyl, alkoxy, halogen, alkyl substituted by halogen or hydroxyl substituents. Preferably the term "optionally substituted hydrocarbon group" refers to an alkyl substituent having one or two substituents selected from alkyl, alkoxy or halogen.

The term "hydrophobic amino acid" includes L- and D-α-amino acids with hydrophobic side chains. The hydrophobic side chains are directly attached to the α-carbon atom of the amino acids. In preferred embodiments of the present invention the hydrophobic side chain is selected from the following groups:

$C_{2-12}$-alkyl i. e. a linear or branched saturated hydrocarbon substituent having 2 to 12 carbon atoms e. g., ethyl, n-propyl, 2-propyl, n-butyl, tert-butyl and the like;

$C_{2-12}$-alkenyl i. e. a linear or branched unsaturated hydrocarbon substituent having 2 to 12 carbon atoms e. g., vinyl, allyl, and the like;

$C_{3-12}$-cycloalkyl i. e. mono- or polycyclic saturated hydrocarbon substituent having 3 to 12 carbon atoms e. g., cyclopropyl, cyclopentyl, cyclohexyl, norbornyl and the like which is optionally substituted with one or several linear or branched saturated hydrocarbon substituents having 1 to 9 carbon atoms;

$C_{6-12}$-aryl i. e. mono- or polycyclic aromatic hydrocarbon substituent having 6 to 12 carbon atoms e. g., phenyl, 1-naphtyl, 2-naphtyl and the like which is optionally substituted with one or several linear or branched saturated hydrocarbon substituents having 1 to 6 carbon atoms or a C(O)—$C_{1-6}$-alkyl substituent;

$C_{1-12}$-heteroaryl i. e. mono- or polycyclic heteroaromatic hydrocarbon substituent having 1 to 12 carbon atoms e. g., 5-tetrazolyl, 2-pyridinyl, 3-imidazolyl, 3-oxazolyl, 7-chinolinyl, 3-benzothienyl, 3-indolyl and the like which is optionally substituted with one or several linear or branched saturated hydrocarbon substituents having 1 to 6 carbon atoms;

$C_{2-12}$-alkylcycloalkyl i. e. a linear or branched saturated hydrocarbon substituent having 1 to 9 carbon atoms, which is optionally substituted with one or several cycloalkyl substituents having 3 to 11 carbon atoms;

$C_{2-18}$-alkylaryl i. e. a linear or branched saturated hydrocarbon substituent having 1 to 12 carbon atoms, which is optionally substituted with one or several aryl substituents having 6 to 12 carbon atoms;

$C_{2-18}$-alkylaryl i. e. a linear or branched saturated hydrocarbon substituent having 1 to 12 carbon atoms, which is optionally substituted with one or several aryl substituents having 6 to 12 carbon atoms; or $C_{2-18}$-alkylheteroaryl i. e. a linear or branched saturated hydrocarbon substituent having 1 to 12 carbon atoms, which is optionally substituted with one or several heteroaryl substituents having 1 to 12 carbon atoms.

In a particularly preferred embodiment of the present invention the hydrophobic side chain is one of the following groups: phenylmethyl, 3-indolylmethyl, 1-naphthylmethyl, 2-naphthylmethyl, 4,4'-biphenylmethyl, 3-benzothienylmethyl, diphenylmethyl, 4-tert-butyl-phenylmethyl, N-methyl-3-indolylmethyl, 4-benzoyl-phenylmethyl, cyclohexylmethyl, phenyl, n-propyl. Most preferably, the hydrophobic side chain is phenylmethyl substituent.

Preferably, the hydrophobic amino acid has log P value higher than −3.

n-Octanol-water partition coefficient P of the hydrophobic amino acid is defined as ratio of concentrations (mol/volume) of the hydrophobic amino acid in n-octanol and in water. Suitable methods for the measurement of n-octanol-water coefficients are, for instance described in Octanol-Water Partition Coefficients: Fundamentals and Physical Chemistry, John Wiley and Sons Ltd., 1997, ISBN: 0-417-97397 1.

Both solvents are mutually saturated before the measurement. At equilibrium the n-octanol phase contains 2.3 mol/L of water and the aqueous phase contains $4.5 \times 10_{-3}$ mol/L of n-octanol. The measurement is carried out at the isoelectric point of the hydrophobic amino acid at temperature of 298 K.

The n-octanol-water coefficient P of the hydrophobic amino acid is preferably determined by the shake-flask method, which is, for example, described in the review of J. Sangster (J. Phys. Chem. Ref. Data 18, 3, pages 1111-1227, 1989). The measurement is carried out under the conditions described by T. Fujita et al (J. Am. Chem. Soc. 86, pages 5175-5180, 1964).

The concentration of the hydrophobic amino acid in the system should be less than 0.01 mol/L in any single phase. Very pure n-octanol and water must be used for the measurement. The system, usually in a separator funnel or similar device, is shaken gently until equilibrium is achieved (0.5 hours to 3 days). The system is then centrifuged to separate the two phases and break any emulsions.

Subsequently, both n-octanol phase and the aqueous phase are analysed to achieve mass balance whereby high-performance liquid chromatography (HPLC) equipped with a suitable reversed-phase column is employed for the analysis.

Alternatively, the n-octanol-water coefficient of the hydrophobic amino acids can be evaluated by using the ALOGPS 2.1 software by I. V. Tetko et al (J. Comput. Aid. Mol. Des. 19, pages 453-63, 2005 and J. Chem. Inf. Comput. Sci. 41, pages 1488-1493, 2001) The software is available from the Virtual Computational Chemistry Laboratory (VC-CLAB, http://www.vcclab.org).

Peptide Structure

The peptide of the present invention has the amino acid sequence $$X^1—X^2—X^3—X^4—X^5—NR^1R^2,$$

wherein
- $X^1$ represents an amino acid selected from the group consisting of Lys, Arg and Gin,
- $X^2$ and $X^4$ each independently represents an aromatic amino acid, with at least one of $X^2$ and $X^4$ being different from D- and L-tryptophane,
- $X^3$ represents a hydrophobic amino acid, and
- $X^5$ represents Leu-Leu,
- $R^1$ and $R^2$ each independently is hydrogen or an optionally substituted hydrocarbon group; or $R^1$ and $R^2$ together with the nitrogen atom to which they are attached form a 5- or 6-membered ring.

In a particularly preferred embodiment of the present invention $R^1$ and $R^2$ are identical and/or are selected from the group consisting of methyl, ethyl and 2-propyl. In yet another preferred embodiment of the present invention $R^1$ and $R^2$ together with the nitrogen atom to which they are attached form a 5- or 6-membered ring selected from the group consisting of pyrrolidine, piperidine or morpholine.

Preferably, $X^1$ is Lys, more preferably $X^1$ is L-Lys.

$X^2$ may be any aromatic amino acid. $X^2$ may for example represent an amino acid selected from the group consisting of D-tryptophane, 1-naphthyl-D-alanine (D-1-Nal), 2-naphthyl-D-alanine (D-2-Nal), D-phenylalanine (D-Phe), 4,4'-biphenyl-D-alanine (D-Bip), β-(3-benzothienyl)-D-alanine (D-Bth), 3,3-diphenyl-D-alanine (D-Dip), tert-butyl-L-phenylalanine (L-tBf), tert-butyl-D-phenylalanine (D-tBf), N-methyl-D-tryptophane (D-Trp(Me)), 4-benzoyl-D-phenylalanine (D-Bpa), 3-cyclohexyl-L-alanine (L-Cha), L-phenylglycine (L-Phg), L-norvaline (L-Nva), and derivatives thereof.

In a preferred embodiment, $X^2$ is an amino acid comprising a bicyclic or dicyclic aromatic side chain.

Examples of $X^2$ include, but are not limited to, compounds of formula (I), (II), (III), (IV) or (V) which are described in the following:

$X^2$ may be an amino acid of formula (I)

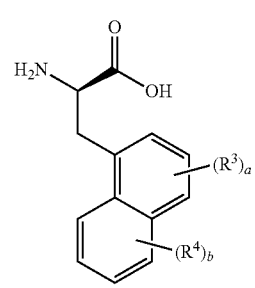

(I)

wherein
each $R^3$ independently is halogen, hydroxyl, CN, $C_1$-$C_2$-alkyl, $C_1$-$C_2$-alkoxy, C(O)—$C_1$-$C_2$-alkyl, C(O)—$C_1$-$C_2$-alkoxy, C(O)NH$_2$, C(O)NH—$C_1$-$C_4$-alkyl, $C_1$-$C_2$-alkyl substituted by halogen;
each $R^4$ independently is is halogen, hydroxyl, CN, $C_1$-$C_4$-alkyl, $C_1$-$C_4$-alkoxy, C(O)—$C_1$-$C_4$-alkyl, C(O)—$C_1$-$C_4$-alkoxy, C(O)NH$_2$, C(O)NH—$C_1$-$C_4$-alkyl, $C_1$-$C_2$-alkyl substituted by halogen, SO$_2$NH$_2$, SO$_2$NH—$C_1$-$C_4$-alkyl;
a is 0, 1, 2;
b is 0, 1, 2, 3, 4;
an amino acid of formula (II)

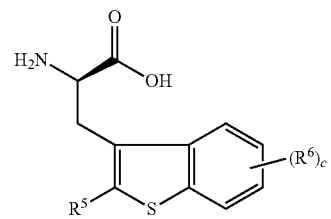

(II)

wherein
$R^5$ is hydrogen, halogen, hydroxyl, CN, $C_1$-$C_2$-alkyl, $C_1$-$C_2$-alkoxy, C(O)—$C_1$-$C_2$-alkyl, C(O)—$C_1$-$C_2$-alkoxy, C(O)NH$_2$, C(O)NH—$C_1$-$C_4$-alkyl, $C_1$-$C_2$-alkyl substituted by halogen;
each $R^6$ independently is halogen, hydroxyl, CN, $C_1$-$C_4$-alkyl, $C_1$-$C_4$-alkoxy, C(O)—$C_1$-$C_4$-alkyl, C(O)—$C_1$-$C_4$-alkoxy, C(O)NH$_2$, C(O)NH—$C_1$-$C_4$-alkyl, $C_1$-$C_2$-alkyl substituted by halogen, SO$_2$NH$_2$, SO$_2$NH—$C_1$-$C_4$-alkyl;
c is 0, 1, 2, 3, 4;
an amino acid of formula (III)

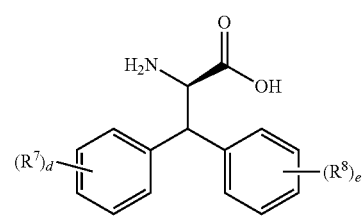

(III)

wherein
each $R^7$ independently is halogen, hydroxyl, CN, $C_1$-$C_4$-alkyl, $C_1$-$C_4$-alkoxy, C(O)—$C_1$-$C_4$-alkyl, C(O)—$C_1$-$C_4$-alkoxy, C(O)NH$_2$, C(O)NH—$C_1$-$C_4$-alkyl, $C_1$-$C_2$-alkyl substituted by halogen, SO$_2$NH$_2$, SO$_2$NH—$C_1$-$C_4$-alkyl;

each R⁸ independently is halogen, hydroxyl, CN, C₁-C₄-alkyl, C₁-C₄-alkoxy, C(O)—C₁-C₄-alkyl, C(O)—C₁-C₄-alkoxy, C(O)NH₂, C(O)NH—C₁-C₄-alkyl, C₁-C₂-alkyl substituted by halogen, SO₂NH₂, SO₂NH—C₁-C₄-alkyl;

d is 0, 1, 2, 3, 4, 5;
e is 0, 1, 2, 3, 4, 5;
an amino acid of formula (IV)

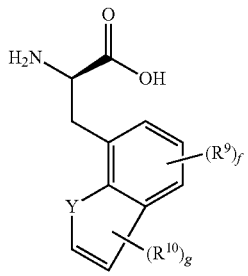

(IV)

wherein
each R⁹ independently is halogen, hydroxyl, CN, C₁-C₂-alkyl, C₁-C₂-alkoxy, C(O)—C₁-C₂-alkyl, C(O)—C₁-C₂-alkoxy, C(O)NH₂, C(O)NH—C₁-C₄-alkyl, C₁-C₂-alkyl substituted by halogen, SO₂NH₂, SO₂NH—C₁-C₂-alkyl;
each R¹⁰ independently is halogen, hydroxyl, CN, C₁-C₄-alkyl, C₁-C₄-alkoxy, C(O)—C₁-C₄-alkyl, C(O)—C₁-C₄-alkoxy, C(O)NH₂, C(O)NH—C₁-C₄-alkyl, C₁-C₂-alkyl substituted by halogen, SO₂NH₂, SO₂NH—C₁-C₄-alkyl;
Y is O, S, NH, N—C₁-C₄-alkyl or CH₂;
f is 0, 1, 2, 3;
g is 0, 1, 2;
or an amino acid of formula (V)

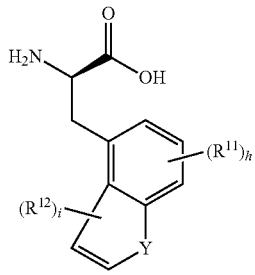

(V)

wherein
each R¹¹ independently is halogen, hydroxyl, CN, C₁-C₂-alkyl, C₁-C₂-alkoxy, C(O)—C₁-C₂-alkyl, C(O)—C₁-C₂-alkoxy, C(O)NH₂, C(O)NH—C₁-C₄-alkyl, C₁-C₂-alkyl substituted by halogen, SO₂NH₂, SO₂NH—C₁-C₂-alkyl;
each R¹² independently is halogen, hydroxyl, CN, C₁-C₄-alkyl, C₁-C₄-alkoxy, C(O)—C₁-C₄-alkyl, C(O)—C₁-C₄-alkoxy, C(O)NH₂, C(O)NH—C₁-C₄-alkyl, C₁-C₂-alkyl substituted by halogen, SO₂NH₂, SO₂NH—C₁-C₄-alkyl;
Y is O, S, NH, N—C₁-C₄-alkyl or CH₂;
h is 0, 1, 2, 3;
i is 0, 1, 2.

In another embodiment of the present invention X² represents an amino acid of the general formula (VI) or of the general formula (VII) below:

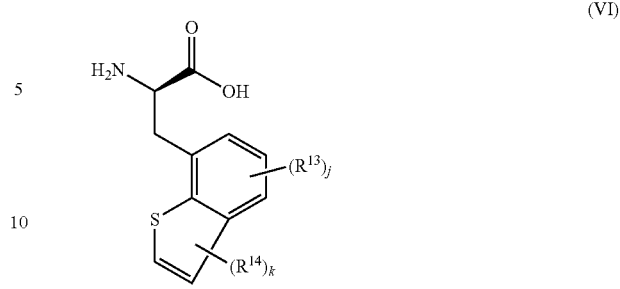

(VI)

wherein
each R¹³ independently is halogen, hydroxyl, CN, C₁-C₂-alkyl, C₁-C₂-alkoxy, C(O)—C₁-C₂-alkyl, C(O)—C₁-C₂-alkoxy, C(O)NH₂, C(O)NH—C₁-C₄-alkyl, C₁-C₂-alkyl substituted by halogen, SO₂NH₂, SO₂NH—C₁-C₂-alkyl;
each R¹⁴ independently is halogen, hydroxyl, CN, C₁-C₄-alkyl, C₁-C₄-alkoxy, C(O)—C₁-C₄-alkyl, C(O)—C₁-C₄-alkoxy, C(O)NH₂, C(O)NH—C₁-C₄-alkyl, C₁-C₂-alkyl substituted by halogen, SO₂NH₂, SO₂NH—C₁-C₄-alkyl;
j is 0, 1, 2, 3;
k is 0, 1, 2.

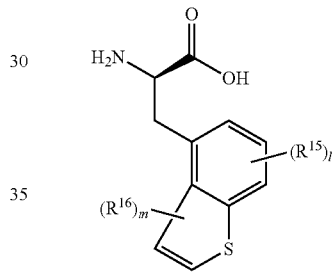

(VII)

wherein
each R¹⁵ independently is halogen, hydroxyl, CN, C₁-C₂-alkyl, C₁-C₂-alkoxy, C(O)—C₁-C₂-alkyl, C(O)—C₁-C₂-alkoxy, C(O)NH₂, C(O)NH—C₁-C₄-alkyl, C₁-C₂-alkyl substituted by halogen, SO₂NH₂, SO₂NH—C₁-C₂-alkyl;
each R¹⁶ independently is halogen, hydroxyl, CN, C₁-C₄-alkyl, C₁-C₄-alkoxy, C(O)—C₁-C₄-alkyl, C(O)—C₁-C₄-alkoxy, C(O)NH₂, C(O)NH—C₁-C₄-alkyl, C₁-C₂-alkyl substituted by halogen, SO₂NH₂, SO₂NH—C₁-C₄-alkyl;
l is 0, 1, 2, 3;
m is 0, 1, 2.

According to a preferred aspect of the invention, X² represents an aromatic amino acid of formula (I) as shown above, wherein
each R³ independently is halogen or hydroxyl,
each R⁴ independently is halogen, hydroxyl,
a is 0, 1;
b is 0, 1, 2, 3;
or an aromatic amino acid of formula (II) as shown above, wherein
each R⁵ independently is hydrogen, halogen or hydroxyl,
each R⁶ independently is halogen, hydroxyl,
c is 0, 1, 2;
or an aromatic amino acid of formula (III) as shown above, wherein
each R⁷ independently is halogen or hydroxyl,
each R⁸ independently is halogen, hydroxyl,
d is 0, 1, 2, 3;

e is 0, 1, 2, 3;
or an aromatic amino acid of formula (IV) as shown above, wherein
each $R^9$ independently is halogen or hydroxyl,
each $R^{10}$ independently is halogen, hydroxyl,
f is 0, 1, 2;
g is 0, 1;
or an aromatic amino acid of formula (V) as shown above, wherein
each $R^{11}$ independently is halogen or hydroxyl,
each $R^{12}$ independently is halogen, hydroxyl,
h is 0, 1, 2;
i is 0, 1;
or an aromatic amino acid of formula (VI) as shown above, wherein
each $R^{13}$ independently is halogen or hydroxyl,
each $R^{14}$ independently is halogen, hydroxyl,
j is 0, 1, 2;
k is 0, 1;
or an aromatic amino acid of formula (VII) as shown above, wherein
each $R^{15}$ independently is halogen or hydroxyl,
each $R^{16}$ independently is halogen, hydroxyl,
l is 0, 1, 2;
m is 0, 1.

$X^4$ may be any aromatic amino acid, for example an amino acid selected from the group consisting of D-tryptophane, 1-naphthyl-D-alanine (D-1-Nal), 2-naphthyl-D-alanine (D-2-Nal), D-phenylalanine (D-Phe), 4,4'-biphenyl-D-alanine (D-Bip), β-(3-benzothienyl)-D-alanine (D-Bth), 3,3-diphenyl-D-alanine (D-Dip), tert-butyl-L-phenylalanine (L-tBf), tert-butyl-D-phenylalanine (D-tBf), N-methyl-D-tryptophane (D-Trp(Me)), 4-benzoyl-D-phenylalanine (D-Bpa), 3-cyclohexyl-L-alanine (L-Cha), L-phenylglycine (L-Phg) and L-norvaline (L-Nva). Alternatively $X^4$ may be any amino acid as defined for $X^2$ above.

Preferably, $X^2$ is D-tryptophane, D-1-Nal, D-Bth or D-Dip. Most preferably $X^2$ is D-1-Nal or a derivative thereof as defined in formula (I), see above.

In another preferred aspect, $X^4$ is D-tryptophane, D-1-Nal, D-2-Nal or D-Bth.

$X^3$ may be any hydrophobic amino acid, for example an amino acid selected from the group consisting of L-phenylalanine, D-tryptophane, 1-naphthyl-D-alanine (D-1-Nal), 2-naphthyl-D-alanine (D-2-Nal), D-phenylalanine (D-Phe), 4,4'-biphenyl-D-alanine (D-Bip), β-(3-benzothienyl)-D-alanine (D-Bth), 3,3-diphenyl-D-alanine (D-Dip), tert-butyl-L-phenylalanine (L-tBp), tert-butyl-D-phenylalanine (D-tBf), N-methyl-D-tryptophane (D-Trp(Me)), 4-benzoyl-D-phenylalanine (D-Bpa), 3-cyclohexyl-L-alanine (L-Cha), L-phenylglycine (L-Phg) and L-norvaline (L-Nva). Most preferably, $X^3$ is L-phenylanaline.

In another embodiment, the invention relates to a peptide comprising the amino acid sequence

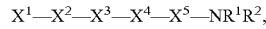

wherein
$X^1$ is Lys,
$X^2$ is an aromatic amino acid other than D- and L-tryptophane,
$X^3$ is L-phenylalanine,
$X^4$ is D-tryptophane,
$X^5$ is Leu-Leu and
$R^1$ and $R^2$ are as defined above.

According to this embodiment $X^2$ has the same meaning as defined above. Preferably, the peptide of this embodiment is an inverse agonist and inhibits the constitutive activity of the ghrelin receptor by at least 10%, preferably by at least 20%, more preferably by at least 30%, more preferably by at least 40%, more preferably by at least 50%, more preferably by at least 60%, most preferably by at least 70%, when determined in an inositol turnover assay in COS-7 cells transfected with the ghrelin receptor ($E_{max}$).

The peptide of this embodiment preferably has an $EC_{50}$ value of less than $10^{-7}$ M, more preferably of less than $5 \times 10^{-8}$ M, more preferably of less than $10^{-8}$ M.

In yet another embodiment the present invention relates to a peptide comprising the amino acid sequence

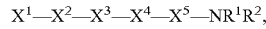

wherein
$X^1$ is L-lysine,
$X^2$ is D-tryptophane,
$X^3$ is L-phenylalanine,
$X^4$ is an aromatic amino acid other than D- and L-tryptophane,
$X^5$ is Leu-Leu and
$R^1$ and $R^2$ are as defined above.

According to this embodiment $X^4$ has the same meaning as defined above. Preferably, the peptide according to this embodiment is an agonist, i.e. it is capable of increasing the constitutive activity of the ghrelin receptor.

Preferably, the efficacy ($E_{max}$) of the peptide according to this embodiment is at least 10%, preferably at least 20%, preferably at least 30%, more preferably at least 40%, more preferably at least 50%, more preferably at least 60%, more preferably at least 70%, more preferably at least 80%, more preferably at least 90%, most preferably at least 100%.

It is further preferred that the $EC_{50}$ value of the peptide of this embodiment is less than $10^{-7}$ M more preferably of less than $5 \times 10^{-8}$ M, more preferably of less than $10^{-8}$ M.

In yet another embodiment the present invention relates to a peptide comprising the amino acid sequence

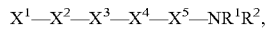

wherein
$X^1$ is lysine,
$X^2$ is an aromatic amino acid different from D-tryptophane,
$X^3$ is L-phenylalanine,
$X^4$ is an aromatic amino acid different from D-tryptophane,
$X^5$ is Leu-Leu and
$R^1$ and $R^2$ are as defined above.

According to this embodiment $X^2$ and $X^4$ have the same meaning as defined above. Preferably, the peptides of this embodiment are inverse agonists.

In yet another embodiment the present invention relates to a peptide comprising the amino acid sequence

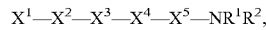

wherein
$X^1$ is lysine,
$X^2$ is D-tryptophane, 1-naphthyl-D-alanine or a derivative thereof as defined above,
$X^3$ is a hydrophobic amino acid other than L-phenylalanine and alanine,
$X^4$ is D-tryptophane
$X^5$ is Leu-Leu and
$R^1$ and $R^2$ are as defined above.

According to this embodiment $X^3$ has the same meaning as defined above.

All of the above-described structural embodiments can be combined with the functional features described hereinafter.

Efficacy and Potency

The $E_{max}$ of the peptide is typically at least 10%, preferably at least 20%, more preferably at least 30%, more preferably at least 40%, more preferably at least 50%, more preferably at least 60%, most preferably at least 70%.

The $EC_{50}$ value of the peptide of the invention is typically less than $10^{-6}$ M, preferably less than $10^{-7}$ M, more preferably less than $5\times10^{-8}$ M, more preferably less than $2\times10^{-8}$ M, most preferably less than $10^{-8}$ M.

Inverse Agonists

In one embodiment, the peptide of the invention is an inverse agonist at the ghrelin receptor. That is, the peptide is capable of decreasing the constitutive activity of the ghrelin receptor. The inverse agonist of the invention is typically capable of decreasing the constitutive activity of the ghrelin receptor by at least 10%, preferably by at least 25%, more preferably by at least 40%, more preferably by at least 50%, even more preferably by at least 60%, most preferably by at least 70%, when contacted with the ghrelin receptor at a concentration of $10^{-6}$ M.

According to a preferred aspect, the inverse agonist of the present invention is capable of decreasing the constitutive activity of the ghrelin receptor by at least 10%, preferably by at least 25%, more preferably by at least 40%, more preferably by at least 50%, even more preferably by at least 60%, most preferably by at least 70%, when contacted with the ghrelin receptor at a concentration of $10^{-7}$ M.

In another preferred aspect, the inverse agonist of the present invention is capable of decreasing the constitutive activity of the ghrelin receptor by at least 10%, preferably by at least 25%, more preferably by at least 40%, more preferably by at least 50%, even more preferably by at least 60%, most preferably by at least 70%, when contacted with the ghrelin receptor at a concentration of $10^{-8}$ M.

With respect to inverse agonists, the maximum inhibition of the constitutive activity of the ghrelin receptor is typically at least 10%, preferably at least 20%, more preferably by at least 30%, more preferably by at least 40%, more preferably by at least 50%, more preferably by at least 60%, more preferably by at least 70%.

Agonists

In a second embodiment, the peptide of the invention is an agonist, i.e. it is capable of increasing the constitutive activity of the ghrelin receptor. According to a preferred aspect of this embodiment, the peptide is capable of increasing the constitutive activity of the ghrelin receptor by at least 10%, more preferably by at least 25%, more preferably by at least 40%, more preferably by at least 50%, more preferably by at least 65%, more preferably by at least 80%, more preferably by at least 90%, most preferably by at least 100%, when contacted with the ghrelin receptor at a concentration of $10^{-6}$ M. This preferably refers to an inositol turnover assay using COS-7 cells transfected with the ghrelin receptor, as described supra.

In another aspect of this embodiment, the peptide is capable of increasing the constitutive activity of the ghrelin receptor by at least 10%, more preferably by at least 25%, more preferably by at least 40%, more preferably by at least 50%, more preferably by at least 65%, more preferably by at least 80%, more preferably by at least 90%, most preferably by at least 100%, when contacted with the ghrelin receptor at a concentration of $10^{-7}$ M.

In another aspect of this embodiment, the peptide is capable of increasing the constitutive activity of the ghrelin receptor by at least 10%, more preferably by at least 25%, more preferably by at least 40%, more preferably by at least 50%, more preferably by at least 65%, more preferably by at least 80%, more preferably by at least 90%, most preferably by at least 100%, when contacted with the ghrelin receptor at a concentration of $10^{-8}$ M.

The efficacy of the agonist peptide relative to the constitutive activity of the ghrelin receptor ($E_{max}$) is typically at least 10%, preferably at least 30%, more preferably at least 50%, more preferably at least 75%, most preferably at least 100%.

Synthesis

The peptides of the present invention can be synthesized using traditional solution synthesis techniques or solid phase chemistry methods. Suitable methods are described in, e.g., Methods of Organic Chemistry, Volume E22: Synthesis of Peptides and Peptidomimetics; Thieme, $4^{th}$ revised ed., ISBN-10: 3131255145, ISBN-13: 978-3131255143.

Pharmaceutical Compositions

The peptides of the present invention or pharmacologically acceptable salts thereof according to the invention may be formulated into pharmaceutical compositions of various dosage forms. To prepare the pharmaceutical compositions of the invention, one or more compounds, including optical isomers, enantiomers, diastereomers, racemates or stereochemical mixtures thereof, or pharmaceutically acceptable salts thereof as the active ingredient is mixed with appropriate carriers and additives according to techniques known to those skilled in the art.

A pharmaceutically acceptable salt refers to a salt form of the compounds of the present invention in order to permit their use or formulation as pharmaceuticals and which retains the biological effectiveness of the free acids and bases of the specified compound and that is not biologically or otherwise undesirable. Examples of such salts are described in Handbook of Pharmaceutical Salts: Properties, Selection, and Use, Wermuth, C. G. and Stahl, P. H. (eds.), Wiley-Verlag Helvetica Acta, Zurich, 2002 [ISBN 3-906390-26-8]. Examples of such salts include alkali metal salts and addition salts of free acids and bases.

If the peptide is a base, a desired salt may be prepared by any suitable method known to those skilled in the art, including treatment of the free base with an inorganic acid. If the peptide is an acid, a desired salt may be prepared by any suitable method known to the art, including treatment of the free acid with an inorganic or organic base, such as an amine (primary, secondary, or tertiary); an alkali metal or alkaline earth metal hydroxide; or the like.

The carriers and additives used for such pharmaceutical compositions can take a variety of forms depending on the anticipated mode of administration. Thus, compositions for oral administration may be, for example, solid preparations such as tablets, sugar-coated tablets, hard capsules, soft capsules, granules, powders and the like, with suitable carriers and additives being starches, sugars, binders, diluents, granulating agents, lubricants, disintegrating agents and the like. Because of their ease of use and higher patient compliance, tablets and capsules represent the most advantageous oral dosage forms for many medical conditions. Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like. Typical preparations for parenteral administration comprise the active ingredient with a carrier such as sterile water or parenterally acceptable oil including polyethylene glycol, polyvinyl pyrrolidone, lecithin, arachis oil or sesame oil, with other additives for aiding solubility or preservation may also be included. In the case of a solution, it can be lyophilized to a powder and then reconstituted immediately prior to use. For dispersions and suspensions, appropriate carriers and additives include aqueous gums, celluloses, silicates or oils.

The pharmaceutical compositions according to embodiments of the present invention include those suitable for oral, rectal, inhalation (e.g., via an aerosol), buccal (e.g., sub-lingual), vaginal, topical (i.e., both skin and mucosal surfaces, including airway surfaces), transdermal administration and parenteral (e.g., subcutaneous, intramuscular, intradermal, intraarticular, intrapleural, intraperitoneal, intrathecal, intracerebral, intracranially, intraarterial, or intravenous), although the most suitable route in any given case will depend on the nature and severity of the condition being treated and on the nature of the particular active agent which is being used.

In some embodiments, the composition is provided in a unit dosage form such as a tablet or capsule. In further embodiments, the present invention provides kits including one or more containers comprising pharmaceutical dosage units comprising an effective amount of one or more compounds of the present invention.

The present invention further provides prodrugs comprising the compounds described herein. The term "prodrug" is intended to mean a compound that is converted under physiological conditions or by solvolysis or metabolically to a specified compound that is pharmaceutically active. The "prodrug" can be a compound of the present invention that has been chemically derivatized such that, (i) it retains some, all or none of the bioactivity of its parent drug compound, and (ii) it is metabolized in a subject to yield the parent drug compound. The prodrug of the present invention may also be a "partial prodrug" in that the compound has been chemically derivatized such that, (i) it retains some, all or none of the bioactivity of its parent drug compound, and (ii) it is metabolized in a subject to yield a biologically active derivative of the compound. Known techniques for derivatizing compounds to provide prodrugs can be employed. Such methods may utilize formation of a hydrolyzable coupling to the compound.

Therapeutic Uses

The invention further pertains to the therapeutic and/or prophylactic use of a peptide described herein. The compounds of the present invention can be used for the prevention and/or treatment of a range of conditions including, but not limited to, metabolic and/or endocrine disorders, obesity and obesity-associated disorders, appetite or eating disorders, addictive disorders, cardiovascular disorders, gastrointestinal disorders, cirrhosis, chronic liver disease and combinations thereof.

Metabolic and/or endocrine disorders include, but are not limited to, obesity, diabetes, in particular, type II diabetes, metabolic syndrome, non-alcoholic fatty liver disease (NAFLD), non-alcoholic steatohepatitis (NASH) and steatosis. Obesity and obesity-associated disorders include, but are not limited to, retinopathy, hyperphagia and disorders involving regulation of food intake and appetite control in addition to obesity being characterized as a metabolic and/or endocrine disorder. Appetite or eating disorders include, but are not limited to, Prader-Willi syndrome and hyperphagia. Addictive disorders include, but are not limited to, alcohol dependence or abuse, illegal drug dependence or abuse, prescription drug dependence or abuse and chemical dependence or abuse (non-limiting examples include alcoholism, narcotic addiction, stimulant addiction, depressant addiction and nicotine addiction). Cardiovascular disorders include, but are not limited to, hypertension and dyslipidemia. Gastrointestinal disorders include, but are not limited to, irritable bowel syndrome, dyspepsia, opioid-induced bowel dysfunction and gastroparesis.

For example, the peptides of the invention may be used to treat conditions associated with or caused by abnormal food intake. The inverse agonists of the present invention are particularly useful in preventing and/or treating disorders such as obesity, overweight, metabolic syndrome, insulin resistance, dyslipidemia, impaired glucose tolerance and hypertension.

The inverse agonists of the present invention may further be used to treat or prevent a chemical substance addiction related disorder, e.g. an alcohol addiction, cocaine addiction, amphetamine addiction, heroin addiction, and nicotine addiction.

The agonists of the present invention are useful in treating and/or preventing conditions such as anorexia and/or abnormally reduced food intake behaviour.

Furthermore, the invention concerns the use of an inverse agonist of the invention or a pharmaceutically acceptable salt thereof for modifying the feeding behaviour or a mammal and/or suppressing hunger or reducing energy intake of a mammal, or for any other of the above conditions.

A pharmaceutical composition of the invention typically comprises a suitable dose of the inverse agonist. The composition may further contain an antagonist to the ghrelin receptor or any other suitable therapeutically or prophylactically active substance. Those of skill in the art will know how to determine an efficient daily dose and, optionally, provide multiple administrations per day. Typically the daily dose is in a range of 0.1 mg to 500 mg daily.

The patient to be treated by the inverse agonist of the invention may have a body mass index of at least 25 kg/m$^2$. Patients who suffer from obesity have a body mass index which is at least about 30 kg/m$^2$.

EXAMPLES

Materials & Methods

Materials.

N$^\alpha$-Fmoc-protected amino acids were purchased from Bachem (Bubendorf, Switzerland) and Iris Biotech GmbH (Marktredwitz, Germany). The used side-chain protecting group for Lys and Trp was tert-butyloxycarbonyl (Boc). The 4-(2',4'-dimethoxyphenyl-9-fluorenylmethoxycarbonyl-aminomethyl)-phenoxy (Rink amide) resin and 1-hydroxybenzotriazole were purchased from Novabiochem (Schwalbach, Germany). N'N'-diisopropylcarbodiimide and acetonitrile (for HPLC) were purchased from Sigma-Aldrich (Taufkirchen, Germany). Trifluoroacetic acid (TFA), f-butanol, methanol, thioanisole, 1,2-ethandithiol were obtained from Fluka (Taufkirchen, Germany). Diethyl ether, dichloromethane, methanol and dimethylformamide were purchased from Biosolve (Valkenswaard, The Netherlands).

For cell culture and inositol trisphosphate turnover assay, the following media and supplements are used: DMEM with higher glucose (4.5 g/l) with L-glutamine, phosphate buffered saline (PBS), BSA, penicillin and streptomycin were purchased from PAA laboratories (Pasching, Austria). Hygromycin B was obtained from InvivoGen Europe (Toulouse, France). Trypsin-EDTA and fetal calf serum (FCS) were obtained from Gibco Life Technologies (Basel, Switzerland). Metafectene™ was purchased from Biontex Laboratories GmbH (Martinsried, Germany). [2-$^3$H(N)]-myo-inositol was obtained from PerkinElmer (Rodgau, Germany). Sodium hydroxide (NaOH) and formic acid (HCOOH) were purchased from Grossing GmbH (Filsum, Germany). Sodium formate (Na-formate) and sodium tetraborate (Na-borate) were obtained from MERCK (Darmstadt, Germany). Sodium-EDTA was purchased from AppliChem (Darmstadt, Germany). Lithium chloride (LiCl) was from Sigma (Taufkirchen, Germany). Ammonium formate was obtained from Paul Lohmann GmbH (Emmerthal, Germany).

Peptide Synthesis.

The synthesis of the peptides was realized on solid support with an automated multiple peptide sequencer (Syro, MultiSynTech, Bochum, Germany) by using the Rink amide resin (21 mg, resin loading: 0.63 mmol/g) and Fmoc/f-Bu strategy as described recently[19]. Special amino acids were coupled with 5 eq. Fmoc amino acid, 5 eq. DIC and 5 eq. HOBt in DMF. The elongated peptides were cleaved from the resin in one step with 90% TFA and scavenger (thioanisole/ethandithiole 7:3 (v/v)) and precipitated with ice-cold mixture of hexane/diethyl ether (3:1 (v/v)). After washing steps, the peptides were finally lyophilized. Purification of the peptides was achieved with preparative HPLC on a reverse-phase C18 column (Phenomenex Jupiter 10u Proteo 90 Å: 250×21.2 mm; 7.78 μm; 90 Å) with a flow rate of 10 ml/min and λ=220 nm. A linear gradient solvent B in solvent A (solvent A: water+0.1% TFA, solvent B: acetonitrile+0.08% TFA) was used depending on the peptides. Peptides were analyzed by MALDI-MS (Ultraflexll, Bruker, Bremen, Germany) and by analytical reverse-phase HPLC on columns Varitide RPC (Varian: 250×4.6 mm; 6 μm; 200 Å) and Phenomenex Jupiter 4u Proteo 90 Å (Phenomenex: 250×4.6 mm; 4 μm; 90 Å). A linear gradient of 20%-70% B in A in 40 min (solvent A: water+0.1% TFA, solvent B: acetonitrile+0.08% TFA) with a flow rate of 0.8 ml/min or 0.6 ml/min was used (λ=220 nm), respectively. The observed masses were in full agreement with the calculated masses and peptides with a purity ≥95% could be obtained according to the analytical HPLC.

Molecular Biology.

The human ghrelin receptor DNA was obtained in pcDNA3.1 vector (Mike Brownstein, NIH, Maryland, USA). Receptor DNA was cloned into pEYFP-N1 (Clontech Europe, Heidelberg, Germany) in order to fuse EYFP C-terminally to the receptor with appropriate restriction endonucleases (SalI and BamHI). The ghrelin receptor EYFP fusion gene was subcloned into the eukaryontic expression plasmid pVitro2-hygro-mcs (InvivoGen Europe, Toulouse, France) via SalI and AvrII. The sequence was verified by sequencing.

Cell Culture and Transfection.

Peptides were tested in COS-7 cells, either transiently or stably transfected with the ghrelin receptor. $EC_{50}$ values and efficacy of peptides tested with the stable or transiently tranfected cells were comparable. COS-7 cells were grown in a humidified atmosphere at 37° C. and 5% $CO_2$ in Dulbecco's modified Eagle's medium with higher glucose supplemented with 10% (v/v) FCS and 1% (v/v) penicillin/streptomycin. COS-7 cells were seeded out in 24-well plates (80.000-100.000 cells/well) in DMEM with 10% FCS. For stable cells, the medium contained 0.4 mg/ml hygromycin B. For transient transfection, COS-7 cells were incubated 14 h with the ghrelin receptor DNA. Each well was treated with 0.3 μg DNA and 0.9 μl metafectene.

Inositol Trisphosphate Turnover Assay.

The day after transfection, or the day after seeding for stable cells, cells were incubated with myo-[2-$^3$H]-inositol (2 μCi/ml) for 18 h and washed with DMEM/LiCl. Stimulation was then carried out with seven to nine different peptide concentrations in DMEM containing 10 mM LiCl, for 2 h, in duplicates. Stimulation was stopped by aspirating the medium and subsequently, cells were lysed with 150 μl of 0.1M NaOH for 5 min at RT. 50 μl of 0.2M HCOOH were added and the solution was diluted using 1 ml dilution buffer. After removing cell debris, the supernatant was purified on an anion-exchange resin (Bio-Rad AG 1-X$^8$) as described recently[19]. Obtained data was analyzed with GraphPad Prism 3.0 (GraphPad Software). Therefore, dpm values are assigned to the corresponding peptide concentrations. Non-linear regression was used to obtain sigmoidal curves. For better comparability, dpm values were normalized to the constitutive activity. Constitutive activity of 100% represents the basal activity, the activity of the receptor without the influence of peptides. $E_{max}$ is the efficacy of the peptide and represents the difference between constitutive activity and activity at maximal effect of the peptide. $EC_{50}$ is the peptide concentration at half-maximal effect.

Animal Studies

For in vivo studies, peptide 3 was delivered intracerebroventricularly. The rats were stereotaxically implanted with a stainless steel cannula (Holm Finmekanik AS, Copenhagen, Denmark) aimed at the right lateral ventricle 1 mm caudal and 1.5 mm lateral to bregma and 4 mm ventral to cranium externa. Rats were left to recover in the metabolic cages (MANI Feed Win, Ellegaard Systems) for adaptation for at least 5 days, only interrupted by daily handling and body weight measurements. With these cages we could accurately measure the food and water intake of rats for up to 48 hours. The powdered diet used eliminated food hoarding and spill. Cannula placement was confirmed by measuring the drinking response to angiotensin injection (100 nmol/rat). Administration of peptide was done with 1 nmol/rat (n=6). As a negative control, a vehicle solution of 0.9% saline with DMSO (n=7) was used.

Results

Peptide Synthesis of KwFwLL-NH$_2$ Analogs.

Figure 2:
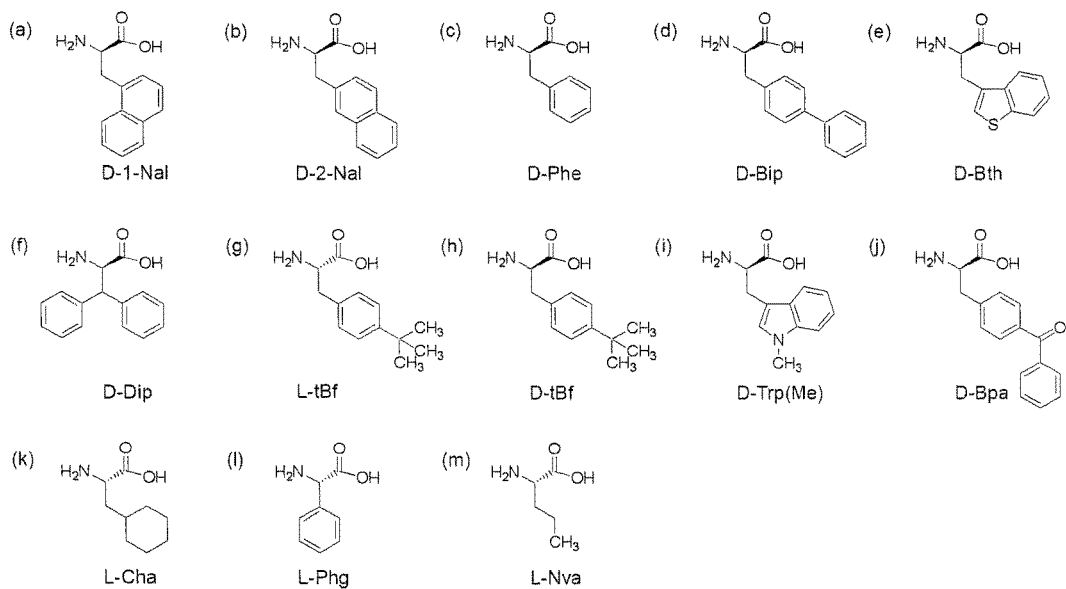
FIG. 2: Chemical structures of non-proteinogenic amino acids used to synthesize analogs of KwFwLL-NH$_2$. (a) 1-naphthyl-D-alanine (D-1-Nal), (b) 2-naphthyl-D-alanine (D-2-Nal), (c) D-phenylalanine (D-Phe), (d) 4,4'-biphenyl-D-alanine (D-Bip), (e) β-(3-benzothienyl)-D-alanine (D-Bth), (f) 3,3-diphenyl-D-alanine (D-Dip), (g) tert-butyl-L-phenylalanine (L-tBf), (h) tert-butyl-D-phenylalanine (D-tBf), (i) N-methyl-D-tryptophane (D-Trp(Me)), (j) 4-benzoyl-D-phenylalanine (D-Bpa), (k) cyclohexyl-L-alanine (L-Cha), (l) L-phenylglycine (L-Phg) and (m) L-norvaline (L-Nva).

The aromatic core -wFw- was described, besides the C-terminal carboxyamide, to be the important recognition motif for binding the ghrelin receptor. KwFwLL-NH$_2$ analogs were synthesized on solid support. Therefore, Rink amide resin was used for solid phase peptide synthesis to release C-terminal amidated peptides. The aromatic peptide core was modified with various aromatic and non-aromatic amino acids to evaluate the influence of aromaticity, size and orientation on peptide activity and efficacy (FIG. 2). All peptides could be synthesized with purity of or higher than 95% (Table 1).

TABLE 1

Analytical data of synthesized peptides.

| No | Peptide | Mass (calc), Da | Mass (exp), Da | % B$^a$ | % B$^b$ | purity |
| --- | --- | --- | --- | --- | --- | --- |
| 1 | Ghrelin | 3368.9 | 3369.8 | 37.4 | 41.0 | >95% |
| 2 | KwFwLL-NH$_2$ | 890.5 | 891.6 | 52.0 | 55.5 | >95% |

TABLE 1-continued

Analytical data of synthesized peptides.

| No | Peptide | Mass (calc), Da | Mass (exp), Da | % B[a] | % B[b] | purity |
|---|---|---|---|---|---|---|
| 3 | K-(D-1-Nal)-FwLL-NH$_2$ | 901.7 | 902.5 | 54.1 | 57.5 | >95% |
| 4 | K-(D-Bth)-FwLL-NH$_2$ | 907.7 | 908.4 | 53.8 | 57.3 | >95% |
| 5 | K-(D-Dip)-FwLL-NH$_2$ | 927.7 | 928.5 | 55.3 | 59.1 | >95% |
| 6 | K-(D-2-Nal)-FwLL-NH$_2$ | 901.7 | 902.6 | 54.0 | 57.4 | >95% |
| 7 | K-(D-Bpa)-FwLL-NH$_2$ | 955.7 | 956.6 | 54.6 | 58.0 | >95% |
| 8 | K-(D-Bip)-FwLL-NH$_2$ | 927.7 | 928.6 | 56.1 | 59.6 | >95% |
| 9 | K-(D-Phe)-FwLL-NH$_2$ | 851.5 | 852.5 | 51.1 | 54.9 | >95% |
| 10 | K-(D-tBf)-FwLL-NH$_2$ | 907.7 | 908.6 | 55.9 | 60.6 | >95% |
| 11 | K-(D-Trp(Me))-FwLL-NH$_2$ | 904.7 | 905.5 | 53.1 | 56.6 | >95% |
| 12 | KwF-(D-1-Nal)-LL-NH$_2$ | 901.7 | 902.7 | 54.9 | 58.3 | >95% |
| 13 | KwF-(D-2-Nal)-LL-NH$_2$ | 901.7 | 902.5 | 54.9 | 58.4 | 95% |
| 14 | KwF-(D-Bip)-LL-NH$_2$ | 927.7 | 928.5 | 56.9 | 60.2 | 95% |
| 15 | KwF-(D-Bpa)-LL-NH$_2$ | 955.7 | 956.5 | 54.6 | 57.8 | >95% |
| 16 | KwF-(D-Dip)-LL-NH$_2$ | 927.7 | 928.7 | 55.6 | 59.4 | >95% |
| 17 | KwF-(D-Bth)-LL-NH$_2$ | 907.7 | 908.6 | 54.9 | 58.4 | >95% |
| 18 | K-(D-1-Nal)-F-(D-1-Nal)-LL-NH$_2$ | 912.9 | 913.6 | 56.9 | 60.6 | >95% |
| 19 | K-(D-1-Nal)-F-(D-Bth)-LL-NH$_2$ | 918.9 | 919.6 | 56.2 | 60.3 | >95% |
| 20 | K-(D-Bth)-F-(D-Bth)-LL-NH$_2$ | 924.9 | 925.5 | 56.1 | 60.2 | >95% |
| 21 | K-(D-1-Nal)-(Cha)-wLL-NH$_2$ | 907.9 | 908.6 | 56.3 | 60.9 | >95% |
| 22 | K-(D-1-Nal)-(L-tBf)-wLL-NH$_2$ | 957.9 | 958.7 | 58.9 | 63.1 | >95% |
| 23 | K-(D-1-Nal)-(D-Phe)-wLL-NH$_2$ | 901.7 | 902.6 | 49.1 | 52.9 | >95% |
| 24 | K-(D-1-Nal)-(L-Nva)-wLL-NH$_2$ | 853.8 | 854.7 | 51.4 | 55.5 | >95% |
| 25 | K-(D-1-Nal)-(L-Phg)-wLL-NH$_2$ | 887.8 | 888.6 | 53.0 | 56.6 | >95% |

[a]Retention time from 20% to 70% ACN (0.08% TFA) in H$_2$O (0.1% TFA) on column Varitide RPC (Varian: 250 × 4.6 mm; 6 μm; 200 Å)
[b]Retention time from 20% to 70% ACN (0.08% TFA) in H$_2$O (0.1% TFA) on C18 column Phenomenex Jupiter 4u Proteo 90 A (Phenomenex: 250 × 4.6 mm; 4 μm; 90 Å)

Annex to Table 1. With reference to the attached sequence listing, the following SEQ ID NOs have been assigned to peptides 2 to 25:

| No | Peptide | SEQ ID NO: |
|---|---|---|
| 2 | KwFwLL-NH$_2$ | 2 |
| 3 | K-(D-1-Nal)-FwLL-NH$_2$ | 3 |
| 4 | K-(D-Bth)-FwLL-NH$_2$ | 4 |
| 5 | K-(D-Dip)-FwLL-NH$_2$ | 5 |
| 6 | K-(D-2-Nal)-FwLL-NH$_2$ | 11 |
| 7 | K-(D-Bpa)-FwLL-NH$_2$ | 12 |
| 8 | K-(D-Bip)-FwLL-NH$_2$ | 13 |
| 9 | K-(D-Phe)-FwLL-NH$_2$ | 14 |
| 10 | K-(D-tBf)-FwLL-NH$_2$ | 15 |
| 11 | K-(D-Trp(Me))-FwLL-NH$_2$ | 16 |
| 12 | KwF-(D-1-Nal)-LL-NH$_2$ | 8 |
| 13 | KwF-(D-2-Nal)-LL-NH$_2$ | 9 |
| 14 | KwF-(D-Bip)-LL-NH$_2$ | 17 |
| 15 | KwF-(D-Bpa)-LL-NH$_2$ | 18 |
| 16 | KwF-(D-Dip)-LL-NH$_2$ | 19 |
| 17 | KwF-(D-Bth)-LL-NH$_2$ | 20 |
| 18 | K-(D-1-Nal)-F-(D-1-Nal)-LL-NH$_2$ | 10 |
| 19 | K-(D-1-Nal)-F-(D-Bth)-LL-NH$_2$ | 6 |
| 20 | K-(D-Bth)-F-(D-Bth)-LL-NH$_2$ | 7 |
| 21 | K-(D-1-Nal)-(Cha)-wLL-NH$_2$ | 21 |
| 22 | K-(D-1-Nal)-(L-tBf)-wLL-NH$_2$ | 22 |
| 23 | K-(D-1-Nal)-(D-Phe)-wLL-NH$_2$ | 23 |
| 24 | K-(D-1-Nal)-(L-Nva)-wLL-NH$_2$ | 24 |
| 25 | K-(D-1-Nal)-(L-Phg)-wLL-NH$_2$ | 25 |

Substitution of w$^2$ in the Aromatic Core Revealed Highly Potent and Efficient Ligands.

Nine analogs (2-11) with the structure KxFwLL-NH$_2$ (Table 2) were synthesized and tested in an inositol trisphosphate turnover assay in COS-7 cells transfected with the ghrelin receptor towards activity and efficacy. The unmodified hexapeptide (peptide 2) showed an efficacy of 37% and an EC$_{50}$ value of 45.6 nM, accordingly to previous reports[17]. In general, substitution of D-Trp with chosen non-natural D-amino acids in the core peptide maintained inverse agonistic activity. The most potent inverse agonists were found by substitution with D-1-Nal (3), D-Bth (4) and D-Dip (5). The peptides were highly active, as they exhibit an activity up to 13.4-fold higher than KwFwLL-NH$_2$. Peptides 6 (D-2-Nal), 7 (D-Bpa), 8 (D-Bip) and 9 (D-Phe) presented a moderate activity. Substitution of D-Trp$^2$ with D-tBf (10) resulted in a severe loss of activity and introduction of D-Trp(Me) (11) led to an inactive compound. Efficacy was significantly increased by all modifications except D-Trp (Me). Notably, peptides 4, 5 and 8 exhibited an efficacy higher 80%.

Both, peptide 11 and peptide 4 have the basic structure of D-Trp with slight modifications. D-Trp(Me) bears a methylation on the nitrogen of the heteroaromatic ring system and in D-Bth, this nitrogen is replaced by a sulphur. Interestingly, whereas peptide 11, containing D-Trp(Me), showed no activity at the ghrelin receptor, substitution with D-Bth (peptide 4) resulted in a 8.0-fold increase in activity and a 2.2-fold increase in efficacy (FIG. 3), representing one of the most potent inverse agonists found in this study.

Figure 3:
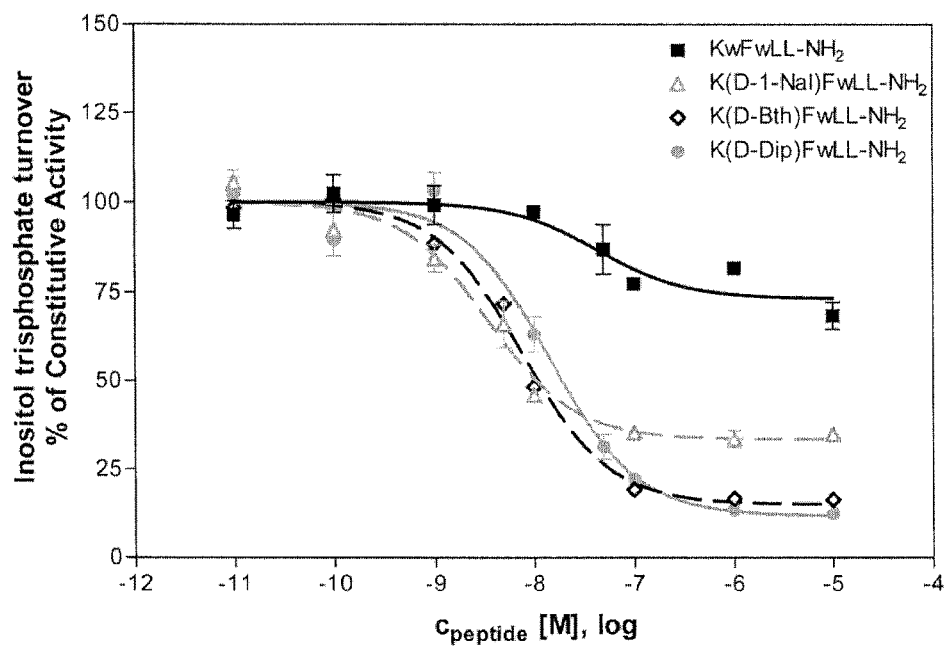
FIG. 3: Sigmoidal concentration-response curves of peptides 2, 3, 4 and 5. Substitution of D-Trp$^2$ with 1-naphthyl-D-alanine, β-(3-benzothienyl)-D-alanine and 3,3-diphenyl-D-alanine increased both, activity and efficacy.

Peptide 9 (D-Phe) presented a moderate EC$_{50}$ of 240.9 nM. Introduction of an aliphatic tert-butyl group in para-position of the Phe (peptide 10, D-tBf) dropped the activity to 624.4 nM. Introduction of D-Dip (5), D-Bpa (7) and D-Bip (8) at position 2 were more advantageous. Indeed, peptide 5 presented a 3.5-fold increase of activity compared with the reference peptide 2 (FIG. 3). Peptides substituted with D-Bip (8) and D-Dip (5) at position 2 showed an efficacy higher 80%.

At last, introduction of both, D-1-Nal (3) and D-2-Nal (6), had a distinct effect and both peptides showed a very different inverse agonist activity at the receptor. Whereas peptide 6 (D-2-Nal) displayed a low activity (161.3 nM), peptide 3 (D-1-Nal) showed a 13.4-fold increase in activity compared with 2 and presented an EC$_{50}$ value of 3.4 nM (FIG. 3), revealing the most potent inverse agonist at the ghrelin receptor. Moreover, we could determine an increase of efficacy for both peptides.

TABLE 2

EC$_{50}$ and efficacy of the analogs KxFwLL-NH2 (2-11) at the ghrelin receptor with respect to inverse agonistic activity. EC$_{50}$ and E$_{max}$ are mean value ± SEM of n experiments. x-fold indicates the shift in potency or efficacy compared to KwFwLL-NH$_2$.

| No | Peptide | EC$_{50}$ ± SEM, nM | x-fold (EC$_{50}$) | E$_{max}$ ± SEM [Δ %] | x-fold (E$_{max}$) | n |
|---|---|---|---|---|---|---|
| 2 | KwFwLL-NH$_2$ | 45.6 ± 0 5.4 | 1 | 37 ± 5 | 1 | 3 |
| 3 | K-(D-1-Nal)-FwLL-NH$_2$ | 3.4 ± 0.4 | 0.07 | 64 ± 2 | 1.7 | 5 |
| 4 | K-(D-Bth)-FwLL-NH$_2$ | 5.7 ± 1.7 | 0.13 | 81 ± 2 | 2.2 | 5 |
| 5 | K-(D-Dip)-FwLL-NH$_2$ | 13.1 ± 1.9 | 0.29 | 87 ± 2 | 2.4 | 4 |
| 6 | K-(D-2-Nal)-FwLL-NH$_2$ | 161.3 ± 32.1 | 3.54 | 66 ± 4 | 1.8 | 2 |
| 7 | K-(D-Bpa)-FwLL-NH$_2$ | 168.6 ± 36.3 | 3.70 | 67 ± 7 | 1.8 | 4 |
| 8 | K-(D-Bip)-FwLL-NH$_2$ | 183.7 ± 97.8 | 4.03 | 82 ± 0 | 2.2 | 3 |
| 9 | K-(D-Phe)-FwLL-NH$_2$ | 240.9 ± 129.1 | 5.28 | 62 ± 4 | 1.7 | 5 |
| 10 | K-(D-tBf)-FwLL-NH$_2$ | 624.4 ± 326.9 | 13.7 | 76 ± 5 | 2.1 | 4 |
| 11 | K-(D-Trp(Me))-FwLL-NH$_2$ | >1000 | >20 | — | — | 2 |

Substitution of w$^4$ in the wFw-Core Eliminates Inverse Agonistic Activity.

Figure 4:
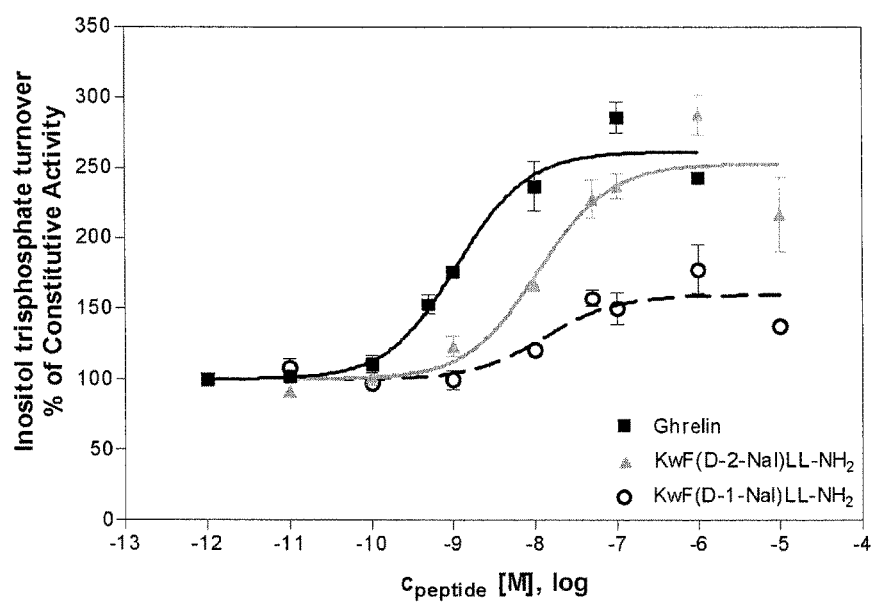
FIG. 4: Sigmoidal concentration-response curves of peptides 1, 12 and 13. With 1-naphthyl-D-alanine and 2-naphthyl-D-alanine at position 4, the hexapeptide showed agonistic activity with EC$_{50}$ values of 17.9 nM and 12.6 nM, respectively.

Besides substitution of w$^2$, replacement of D-Trp residue at position 4 with various aromatic D-amino acids was evaluated (Table 3). Surprisingly, all modifications eliminated inverse agonistic activity. Peptides 14 (D-Bip), 15 (D-Bpa), 16 (D-Dip) and 17 (D-Bth) showed no activity and therefore, acted neither as agonists nor as inverse agonists at the ghrelin receptor. In contrast, with both D-1-Nal (peptide 12) and D-2-Nal (peptide 13) substitutions at position 4, the peptides presented strong agonist potencies. Peptide 12 displayed an EC$_{50}$ value of 17.9 nM and peptide 13 an EC$_{50}$ value of 12.6 nM. Interestingly, peptide 13 exhibited a significant higher E$_{max}$ than peptide 12 (156% to 54%), comparable to the endogenous ligand ghrelin (FIG. 4). Peptide 13 is the most efficient short agonist found so far with a nanomolar activity and presenting 96% of ghrelin efficacy.

TABLE 3

EC$_{50}$ and efficacy of ghrelin (1) and the analogs KwFxLL-NH$_2$ (12-17) at the ghrelin receptor with respect to agonistic activity. EC$_{50}$ and E$_{max}$ are mean value ± SEM of n experiments. x-fold indicates the shift in potency or efficacy compared to ghrelin.

| No | Peptide | EC$_{50}$ ± SEM, nM | x-fold (EC$_{50}$) | E$_{max}$ ± SEM [Δ %] | x-fold (E$_{max}$) | n |
|---|---|---|---|---|---|---|
| 1 | Ghrelin | 1.4 ± 0.2 | 1 | 162 ± 12 | 1 | 8 |
| 12 | KwF-(D-1-Nal)-LL-NH$_2$ | 17.9 ± 6.4 | 12.8 | 54 ± 10 | 0.3 | 3 |
| 13 | KwF-(D-2-Nal)-LL-NH$_2$ | 12.6 ± 2.2 | 9.00 | 156 ± 22 | 1 | 3 |
| 14 | KwF-(D-Bip)-LL-NH$_2$ | >1000 | >700 | — | — | 2 |
| 15 | KwF-(D-Bpa)-LL-NH$_2$ | >1000 | >700 | — | — | 2 |
| 16 | KwF-(D-Dip)-LL-NH$_2$ | >1000 | >700 | — | — | 4 |
| 17 | KwF-(D-Bth)-LL-NH$_2$ | >1000 | >700 | — | — | 3 |

Simultaneous Modifications of D-Trp$^{2,4}$ with D-1-Nal and D-Bth.

Figure 5:
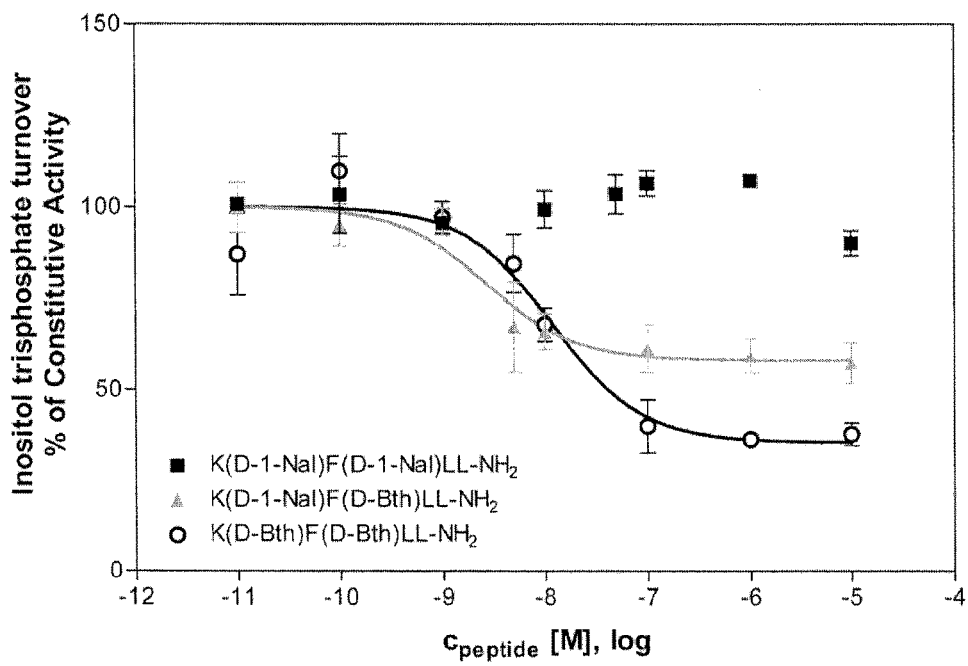
FIG. 5: Sigmoidal concentration-response curves of peptides 18, 19 and 20. Whereas the substitution with 1-naphthyl-D-alanine at both positions led to a significant loss of efficacy, peptides containing β-(3-benzothienyl)-D-alanine maintain inverse agonistic activity, with higher activity and efficacy than KwFwLL-NH$_2$.

For further investigations, the hexapeptide was modified simultaneously on both D-Trp at positions 2 and 4, with either D-1-Nal or D-Bth. Three analogs of KxFxLL-NH$_2$ were synthesized (Table 4). With the introduction of D-1-Nal and D-Bth at position 2 (peptides 3 and 4, respectively), the hexapeptides act as strong inverse agonists. In contrast, introduction of D-1-Nal at position 4 (peptide 12) resulted in a potent agonist with a nanomolar activity. At last, substitution of D-Trp$^4$ with D-Bth (17) led to a total loss of activity. Remarkably, substitution with D-1-Nal at both positions (peptide 18) totally suppressed activity (FIG. 5). In contrast, the introduction of D-Bth at position 4 (peptide 19) or at both positions (peptide 20) led to highly active inverse agonists with EC$_{50}$ values of 2.1 nM and 9.4 nM, respectively. Whereas, peptide 19 showed an efficacy of 40%, the presence of D-Bth in positions 2 and 4 (20) led to a more efficient peptide (E$_{max}$=67%).

TABLE 4

EC$_{50}$ and efficacy of the analogs KxFxLL-NH$_2$ (18-20) at the ghrelin receptor with respect to inverse agonistic activity. EC$_{50}$ and E$_{max}$ are mean value ± SEM of n experiments.

| No | Peptide | EC$_{50}$ ± SEM, nM | E$_{max}$ ± SEM [Δ %] | n |
|---|---|---|---|---|
| 18 | K-(D-1-Nal)-F-(D-1-Nal)-LL-NH$_2$ | >1000 | — | 2 |
| 19 | K-(D-1-Nal)-F-(D-Bth)-LL-NH$_2$ | 2.1 ± 0.6 | 40 ± 2 | 2 |
| 20 | K-(D-Bth)-F-(D-Bth)-LL-NH$_2$ | 9.4 ± 2.6 | 67 ± 2 | 2 |

Substitution of F$^3$ in K(D-1-Nal)FwLL-NH$_2$ Decreased Activity but Maintained or Increased Efficacy.

The significance of the aromatic character at position 3 was evaluated on the optimized ghrelin receptor inverse agonist K-(D-1-Nal)-FwLL-NH$_2$. Five analogs of the hexapeptide K(D-1-Nal)xwLL-NH$_2$ were synthesized (Table 5). In general, a decrease in activity could be observed in comparison to the lead peptide 3. Furthermore, efficacy is maintained or increased.

Figure 6:
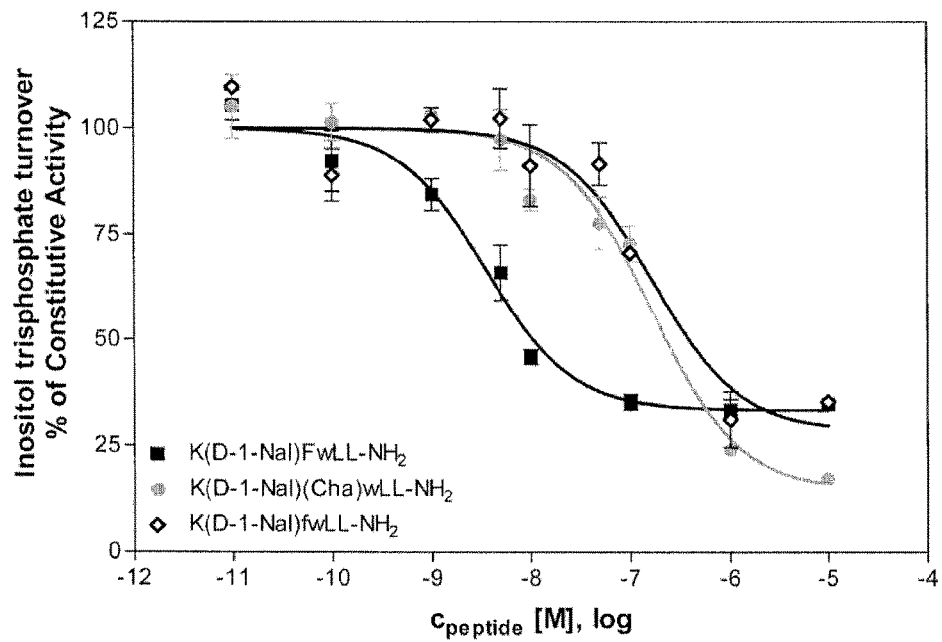
FIG. 6: Sigmoidal concentration-response curves of peptides 3, 21 and 23. Substitution of L-Phe$^3$ with the D-amino acid analog had no effect on efficacy. In contrast, introduction of the non-aromatic, cyclic amino acid 3-cyclohexyl-L-alanine resulted in a significant increase in efficacy.

The substitution of L-Phe at position 3 with its D-analog (D-Phe, peptide 23) resulted in a 35.2-fold loss of activity, but no significant difference in efficacy (FIG. 6). In contrast, the introduction of L-tBf (peptide 22) significantly increased efficacy (E$_{max}$=84%), but had a negative influence on activity. Thus, the additional f-butyl group in para-position at the aromatic benzene ring influenced both, activity and efficacy. The introduction of L-phenylglycine (peptide 25) resulted in a loss of activity with an EC$_{50}$ value higher than 1000 nM.

The replacement of L-Phe$^3$ with non-aromatic amino acids L-Cha (21) and L-Nva (24) decreased activity. Surprisingly, peptide 21 was able to activate the ghrelin receptor in the high nanomolar range and furthermore, efficacy was increased 1.3-fold. Substitution with L-Nva (24), an aliphatic amino acid without π-electrons, led to a very low potency in the submicromolar range and showed efficacy comparable to K(D-1-Nal)FwLL-NH$_2$ (3).

TABLE 5

EC$_{50}$ and efficacy of the analogs K-(D-1-Nal)-xwLL-NH$_2$ (3, 21-25) at the ghrelin receptor with respect to inverse agonistic activity. Substitutions of L-phenylalanine with structural different amino acids lead to a decrease of activity. EC$_{50}$ and E$_{max}$ are mean value ± SEM of n experiments. x-fold indicates the shift of potency or efficacy compared to K-(D-1-Nal)-FwLL-NH$_2$.

| No | Peptide | EC$_{50}$ ± SEM, nM | x-fold (EC$_{50}$) | E$_{max}$ ± SEM [Δ %] | x-fold (E$_{max}$) | n |
|---|---|---|---|---|---|---|
| 3 | K-(D-1-Nal)-FwLL-NH2 | 3.4 ± 0.4 | 1 | 64 ± 2 | 1 | 5 |
| 21 | K-(D-1-Nal)-(L-Cha)-wLL-NH$_2$ | 96.8 ± 33.5 | 28.5 | 85 ± 3 | 1.3 | 3 |
| 22 | K-(D-1-Nal)-(L-tBf)-wLL-NH$_2$ | 124.1 ± 47.4 | 36.5 | 84 ± 3 | 1.3 | 3 |
| 23 | K-(D-1-Nal)-(D-Phe)-wLL-NH$_2$ | 119.6 ± 15.8 | 35.2 | 58 ± 7 | 0.9 | 4 |
| 24 | K-(D-1-Nal)-(L-Nva)-wLL-NH$_2$ | 498.1 ± 250.09 | 146.5 | 71 ± 4 | 1.1 | 3 |
| 25 | K-(D-1-Nal)-(L-Phg)-wLL-NH$_2$ | >1000 | >290 | — | — | 2 |

Animal Studies

Figure 7:
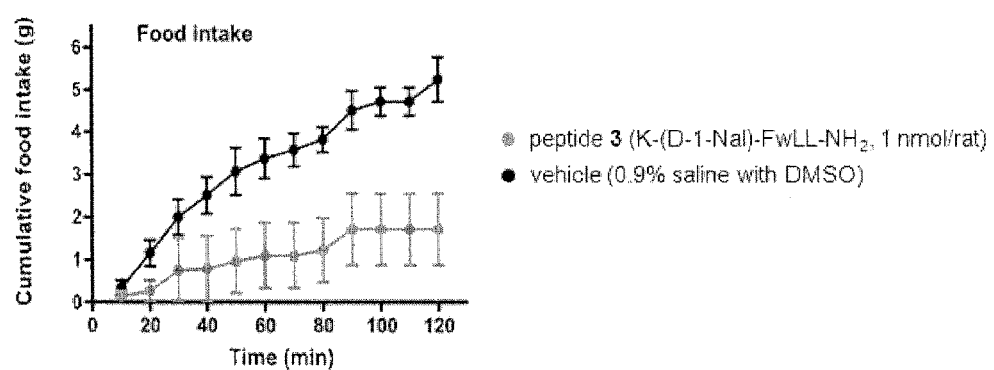
FIG. 7: ICV administration of peptide 3 to rats. The food intake of rats was decreased almost 5-fold in comparison to rats injected with vehicle solution.

Peptide 3 showed the highest inverse agonist potency observed in this study. It presented an EC$_{50}$ value of 3.4 nM and an efficacy of 64%. We therefore tested the ability of this inverse agonist to modulate food intake in rats (FIG. 7). ICV administration of peptide 3 to rats (1 nmol/rat, n=6) decreased the food intake almost 5-fold compared to rats injected with the vehicle solution (0.9% saline with DMSO, n=7) P=0.0077, 2-way ANOVA.

REFERENCES

1. Howard, A. D.; Feighner, S. D.; Cully, D. F.; Arena, J. P.; Liberator, P. A.; Rosenblum, C. I.; Hamelin, M.; Hreniuk, D. L; Palyha, O. C; Anderson, J.; Paress, P. S.; Diaz, C; Chou, M.; Liu, K. K.; McKee, K. K.; Pong, S. S.; Chaung, L. Y.; Elbrecht, A.; Dashkevicz, M.; Heavens, R.; Rigby, M.; Sirinathsinghji, D. J.; Dean, D. C; Melillo, D. G.; Patchett, A. A.; Nargund, R.; Griffin, P. R.; DeMartino, J. A.; Gupta, S. K.; Schaeffer, J. M.; Smith, R. G.; Van der Ploeg, L. H. A receptor in pituitary and hypothalamus that functions in growth hormone release. *Science* 1996, 273, 974-7.
2. Kojima, M.; Hosoda, H.; Date, Y.; Nakazato, M.; Matsuo, H.; Kangawa, K. Ghrelin is a growth-hormone-releasing acylated peptide from stomach. *Nature* 1999, 402, 656-60.
3. Tschop, M.; Smiley, D. L.; Heiman, M. L. Ghrelin induces adiposity in rodents. *Nature* 2000, 407, 908-13.
4. Nakazato, M.; Murakami, N.; Date, Y.; Kojima, M.; Matsuo, H.; Kangawa, K.; Matsukura, S. A role for ghrelin in the central regulation of feeding. *Nature* 2001, 409, 194-8.
5. Lopez, M.; Lage, R.; Saha, A. K.; Perez-Tilve, D.; Vazquez, M. J.; Varela, L.; Sangiao-Alvarellos, S.; Tovar, S.; Raghay, K.; Rodriguez-Cuenca, S.; Deoliveira, R. M.; Castaneda, T.; Datta, R.; Dong, J. Z.; Culler, M.; Sleeman, M. W.; Alvarez, C. V.; Gallego, R.; Lelliott, C. J.; Carling, D.; Tschop, M. H.; Dieguez, C; Vidal-Puig, A. Hypothalamic fatty acid metabolism mediates the orexigenic action of ghrelin. *Cell Metab* 2008, 7, 389-99.
6. Lage, R.; Vazquez, M. J.; Varela, L.; Saha, A. K.; Vidal-Puig, A.; Nogueiras, R.; Dieguez, C; Lopez, M. Ghrelin effects on neuropeptides in the rat hypothalamus depend on fatty acid metabolism actions on BSX but not on gender. *FASEB J* 2010.
7. Wren, A. M.; Seal, L. J.; Cohen, M. A.; Brynes, A. E.; Frost, G. S.; Murphy, K. G.; Dhillo, W. S.; Ghatei, M. A.; Bloom, S. R. Ghrelin enhances appetite and increases food intake in humans. *J Clin Endocrinol Metab* 2001, 86, 5992.
8. Hoist, B.; Holliday, N. D.; Bach, A.; Elling, C. E.; Cox, H. M.; Schwartz, T. W. Common structural basis for constitutive activity of the ghrelin receptor family. *J Biol Chem* 2004, 279, 53806-17.
9. Hoist, B.; Schwartz, T. W. Constitutive ghrelin receptor activity as a signaling set-point in appetite regulation. *Trends Pharmacol Sci* 2004, 25, 113-7.
10. Rokholm, B.; Baker, J. L.; Sorensen, T. I. The levelling off of the obesity epidemic since the year 1999—a review of evidence and perspectives. *Obes Rev* 11, 835-46.
11. Hofbauer, K. G.; Nicholson, J. R. Pharmacotherapy of obesity. *Exp Clin Endocrinol Diabetes* 2006, 114, 475-84.
12. Chollet, C; Meyer, K.; Beck-Sickinger, A. G. Ghrelin—a novel generation of anti-obesity drug: design, pharmacomodulation and biological activity of ghrelin analogues. *J Pept Sci* 2009, 15, 711-30.
13. Cooke, D.; Bloom, S. The obesity pipeline: current strategies in the development of anti-obesity drugs. *Nat Rev Drug Discov* 2006, 5, 919-31.
14. Hatef, D. A.; Trussler, A. P.; Kenkel, J. M. Procedural risk for venous thromboembolism in abdominal contouring surgery: a systematic review of the literature. *Plast Reconstr Surg* 125, 352-62.
15. Berthoud, H. R.; Shin, A. C; Zheng, H. Obesity surgery and gut-brain communication. *Physiol Behav*.
16. Hoist, B.; Cygankiewicz, A.; Jensen, T. H.; Ankersen, M.; Schwartz, T. W. High constitutive signaling of the ghrelin receptor-identification of a potent inverse agonist. *Mol Endocrinol* 2003, 17, 2201-10.
17. Hoist, B.; Lang, M.; Brandt, E.; Bach, A.; Howard, A.; Frimurer, T. M.; Beck-Sickinger, A.; Schwartz, T. W. Ghrelin receptor inverse agonists: identification of an active peptide core and its interaction epitopes on the receptor. *Mol Pharmacol* 2006, 70, 936-46.
18. Hoist, B.; Mokrosinski, J.; Lang, M.; Brandt, E.; Nygaard, R.; Frimurer, T. M.; Beck-Sickinger, A. G.; Schwartz, T. W. Identification of an efficacy switch region in the ghrelin receptor responsible for interchange between agonism and inverse agonism. *J Biol Chem* 2007, 282, 15799-811.

19. Els, S.; Beck-Sickinger, A. G.; Chollet, C. Ghrelin receptor: high constitutive activity and methods for developing inverse agonists. *Methods Enzymol* 485, 103-21.
20. Sylvia Els, Enrico Schild, Pia Steen Petersen, Tom-Marten Kilian, Jacek Mokrosinski, Thomas M. Frimurer, Constance Chollet, Thue W. Schwartz, Birgitte Hoist, Annette G. Beck-Sickinger; An Aromatic Region to Induce a Switch between Agonism and Inverse Agonism at the Ghrelin Receptor; Journal of Medicinal Chemistry, accepted.

The invention claimed is:

1. A peptide comprising the amino acid sequence $$X^1-X^2-X^3-X^4-X^5-NR^1R^2,$$

wherein
- $X^1$ represents an amino acid selected from the group consisting of Lys and Arg;
- $X^2$ is selected from the group consisting of 1-naphthyl-D-alanine (D-1-Nal), β-(3-benzothienyl)-D-alanine (D-Bth) and 3,3-diphenyl-D-alanine (D-Dip) and $X^4$ is D- or L-tryptophane or, alternatively,
- $X^2$ is D- or L-tryptophane and $X^4$ is selected from the group consisting of 1-naphthyl-D-alanine (D-1-Nal) and 2-naphthyl-D-alanine (D-2-Nal), or, alternatively,
- $X^2$ is selected from the group consisting of 1-naphthyl-D-alanine (D-1-Nal), and β-(3-benzothienyl)-D-alanine (D-Bth) and $X^4$ is β-(3-benzothienyl)-D-alanine (D-Bth);
- $X^3$ represents a hydrophobic amino acid selected from the group consisting of L-phenylalanine, D-tryptophane, 1-naphthyl-D-alanine (D-1-Nal), 2-naphthyl-D-alanine (D-2-Nal), D-phenylalanine, 4,4'-biphenyl-D-alanine (D-Bip), β-(3-benzothienyl)-D-alanine (D-Bth), 3,3-diphenyl-D-alanine (D-Dip), tert-butyl-L-phenylalanine (L-tBp), tert-butyl-D-phenylalanine (D-tBf), N-methyl-D-tryptophane (D-Trp(Me)), 4-benzoyl-D-phenylalanine (D-Bpa), 3-cyclohexyl-L-alanine (L-Cha), L-phenylglycine (L-Phg) and L-norvaline (L-Nva);
- $X^5$ represents Leu-Leu; and
- $R^1$ and $R^2$ are each independently hydrogen or an optionally substituted hydrocarbon group; or, alternatively, $R^1$ and $R^2$ together with the nitrogen atom to which they are attached form a 5- or 6-membered ring;

further wherein said peptide is capable of increasing or decreasing the constitutive activity of a ghrelin receptor by at least 10%, when contacted with said ghrelin receptor at a concentration of $10^{-7}$ M in an inositol turnover assay in COS-7 cells expressing the ghrelin receptor.

2. The peptide of claim 1, wherein $X^2$ is selected from the group consisting of 1-naphthyl-D-alanine (D-1-Nal), β-(3-benzothienyl)-D-alanine (D-Bth), and 3,3-diphenyl-D-alanine (D-Dip) and $X^4$ is D- or L-tryptophane.

3. The peptide of claim 1, wherein $X^4$ is selected from the group consisting of 1-naphthyl-D-alanine (D-1-Nal) and 2-naphthyl-D-alanine (D-2-Nal) and $X^2$ is D- or L-tryptophane.

4. The peptide of claim 1, wherein $X^2$ is D-tryptophane and thus $X^4$ is selected from the group consisting of 1-naphthyl-D-alanine (D-1-Nal) and 2-naphthyl-D-alanine (D-2-Nal).

5. The peptide of claim 1, wherein $X^4$ is D-tryptophane and thus $X^2$ is selected from the group consisting of 1-naphthyl-D-alanine (D-1-Nal), β-(3-benzothienyl)-D-alanine (D-Bth) and 3,3-diphenyl-D-alanine (D-Dip).

6. The peptide of claim 1, wherein $X^1$ is Lys.

7. The peptide of claim 1, wherein $X^3$ is L-phenylalanine.

8. The peptide of claim 1, wherein said peptide is capable of decreasing the constitutive activity of said ghrelin receptor by at least 25% at a concentration of $10^{-7}$ M.

9. The peptide of claim 8, wherein said peptide comprises an amino acid sequence selected from the group consisting of SEQ ID NO: 3, 4, 5, 6 and 7.

10. The peptide of claim 8, wherein said peptide is capable of reducing the food intake of a mammal when administered to said mammal.

11. The peptide of claim 1, wherein said peptide is capable of increasing the constitutive activity of said ghrelin receptor by at least 25% at a concentration of $10^{-7}$ M.

12. The peptide of claim 11, wherein said peptide comprises an amino acid sequence selected from the group consisting of SEQ ID NO: 8 or 9.

13. The peptide of claim 11, wherein said peptide is capable of promoting the appetite of a mammal when administered to said mammal.

14. A method of treating or preventing a condition selected from the group consisting of obesity and obesity-associated disorders, appetite or eating disorders, and combinations thereof in a subject in need thereof, said method comprising the step of administering to said subject an effective amount of the peptide according to claim 1.

15. The method of claim 14, wherein said condition is selected from the group consisting of obesity, overweight, metabolic syndrome, insulin resistance, dyslipidemia, impaired glucose tolerance and hypertension.

16. The method of claim 14, wherein said condition is anorexia and/or abnormally reduced food intake behaviour.

17. A pharmaceutical composition comprising the peptide according to claim 1.

* * * * *